United States Patent [19]

Chamoun et al.

[11] Patent Number: 5,320,109
[45] Date of Patent: Jun. 14, 1994

[54] CEREBRAL BIOPOTENTIAL ANALYSIS SYSTEM AND METHOD

[75] Inventors: Nassib G. Chamoun, Dedham; Peter A. Mead; Hsing H. Chiang, both of Brookline; Vikas Saini, Jamaica Plain, all of Mass.

[73] Assignee: Aspect Medical Systems, Inc., Framingham, Mass.

[21] Appl. No.: 782,636

[22] Filed: Oct. 25, 1991

[51] Int. Cl.$^5$ .............................................. A61B 5/048
[52] U.S. Cl. ..................................... 28/731; 128/732; 128/733
[58] Field of Search ........... 128/731, 732, 733, 419 R; 364/413.02

[56] References Cited

U.S. PATENT DOCUMENTS

| | | | |
|---|---|---|---|
| 4,407,299 | 10/1983 | Culver | 128/731 |
| 4,557,270 | 12/1985 | John | 128/731 |
| 4,697,598 | 10/1987 | Bernard et al. | 128/731 |
| 4,705,049 | 11/1987 | John | 128/731 |
| 4,753,246 | 6/1988 | Freeman | 128/731 |

(List continued on next page.)

OTHER PUBLICATIONS

Proceedings of the Fourteenth Annual Northeast Bioengineering Conference, IEEE, New York, US Mar. 10, 1988, Durham, N.H., pp. 198–203, XP000093434, Ning et al., "Detecting Biphase Coupling of Sleep EEG Via Bispectra".

IEEE Transactions on Biomedical Engineering, IEEE, New York, vol. 36, No. 4, Apr. 4, 1989, pp. 497–499, Ning et al, "Bispectral Analysis of the Rat EEG During Various Vigilance States".

IEEE Engineering in Medicine & Biology Society 10th Annual Conference, IEEE New York, vol. 3/4, Nov. 4, 1988, New Orleans, pp. 1218–1291, Ning et al, "Bispectral Analysis of Rat EEG During Maturation".

Withington, P. S., Morton, J., Arnold, R., Sebel, P. S., and Moberg, R. Assessment of power spectral edge for monitoring depth of anesthesia using low methohexitone infusion. Int-J-Clin-Monit-Computing. 3(2): pp. 117–122 (1986).

Whitton, Genetic Dependence of the Electroencephalogram Bispectrum, Electroenceophalogray and Clinical Neurophysiology, 1985, 60: 293–298, Elsevier Scientific Publishers Ireland, Ltd.

Levy, W. J., Intraoperative EEG patterns: implications for EEG monitoring. Anesthesiology. 60(5): pp. 430–434 (1984).

Pichlmayr, I., and Lips, U. EEG Monitoring in anesthesiology and intensive care. Neuropsychobiology, 10(4): pp. 239–248 (1983).

Baker, A. B., and Roxburgh, A. J. Computerised EEG monitoring for carotid endarterectomy, Anaesth-Intensive Care, 14(1): pp. 32–36 (1986).

Brillinger, D. R. An introduction to polyspecta. Annals of Mathematical Statistics 36:1351–74 (1965).

Russ, W., Kling, D., Krumholz, W., Fraedrich, G., and Hempelmann, G., [Experience with a new EEG spectral analyzer in carotid surgery] Erfahrungen mit einem neuen EEG-Spektralanalysator in der Karotischirurgie. Anaesthetist 34(2): pp. 85–90 (1985).

(List continued on next page.)

*Primary Examiner*—William E. Kamm
*Assistant Examiner*—George Manuel
*Attorney, Agent, or Firm*—Hale and Dorr

[57] ABSTRACT

Disclosed is a real time diagnostic apparatus and method quantitatively evaluating, in a noninvasive manner, cerebral phenomena. Surface electroencephalographic (EEG) signals are obtained and filtered in a desired frequency range. Digital EEG data is normalized and the dynamic phase and density relations within the signal are characterized by processing the filtered signals to generate Kth-ordered spectral values where K is an integer greater than 2. A diagnostic index which quantifies the detected cerebral phenomena is then derived from the generated Kth-order spectral values.

45 Claims, 14 Drawing Sheets

U.S. PATENT DOCUMENTS

| | | | |
|---|---|---|---|
| 4,905,285 | 2/1990 | Allen et al. | 128/419 R |
| 4,907,597 | 3/1990 | Chamoun | 128/731 |
| 4,974,602 | 12/1990 | Abraham-Fuchs et al. | 124/731 |
| 5,010,891 | 4/1991 | Chamoun | 128/731 |

OTHER PUBLICATIONS

Rampil, I. J., Holzer, J. A., Quest, D. O., Rosenbaum, S. H., and Correll J. W., Prognostic value of computerized EEG analysis during carotic endarterectomy. Anesthesia Analgesia 62:186–92 (1983).

Huber, P. J., B. Kleiner, T. Gasser and G. Dumermuth, Statistical method for investigating phase relations in stationary stochastic processes, IEEE Trans. Aud. & Electroacou. AU-19/1:78–86 (1971).

Tryon, P. V. The bispectrum and higher–order spectra: A bibliograph. US NBS (Tech Note 1036) (1981).

Nikias, C. L., and Raghuveer, M. R. Bispectrum estimation: A digital signal processing framework, Proc. IEEE 75, 7:869–91 (1987).

Susumu, T. and Osamu, T. Analysis of wave shapes of alpha waves on EEG by means of the bispectrum (1973).

Kleiner, B., Huber, P. J., and Dumermuth, G. Analysis of the interelations between frequency bands of the EEG by means of the bispectrum, Electroencephalogr. Neurophysiol. 27(7): 693–694 (1969).

Dumermuth, G., Huber, P. J., Kleiner, B., and Gasser, T. Analysis of the interrelations between frequency bands of the EEG by means of the bispectrum, A preliminary study, Electroencephalogr. Clin. Neurophysiol. 31(2):137–148 (1971).

Barnett, T. P., Johnson, L. C., Naitoh, P., Hicks, N. and Nute, C., Bispectrum analysis of electroencephalogram signals during waking and sleeping, Science 172:402–401 (1971).

Raghuveer, M. R. and Nikias, C. L. Bispectrum estimation: A parametric approach, IEEE Trans. on Acoustics, Speech & Signal Processing, 33:1213–1230 (1985).

Volavka, J., Matousek, M., Feldstein, S. et al. The reliability of electroencephalography assesement. Electroencephalography and Electromyography, 4: 123 (1973).

Eichhorn, J. H., Cooper, J. B., Cullen, D. J., Ward, M. R., Philip, J. H., and Seeman, R. G. Standards for patient monitoring during anesthesia at Harvard Medical School. JAMA. 256(8): pp. 1017–1020 (1986).

Jasper, H. H. The ten–twenty electrode system of the international federation in electroencephalography and clinical neurophysiology, EEG Journal. 10:371–375 (1985).

Haykin, S. Adaptive filter theory, Prentice–Hall, Englewood Cliffs, N.J., (1986).

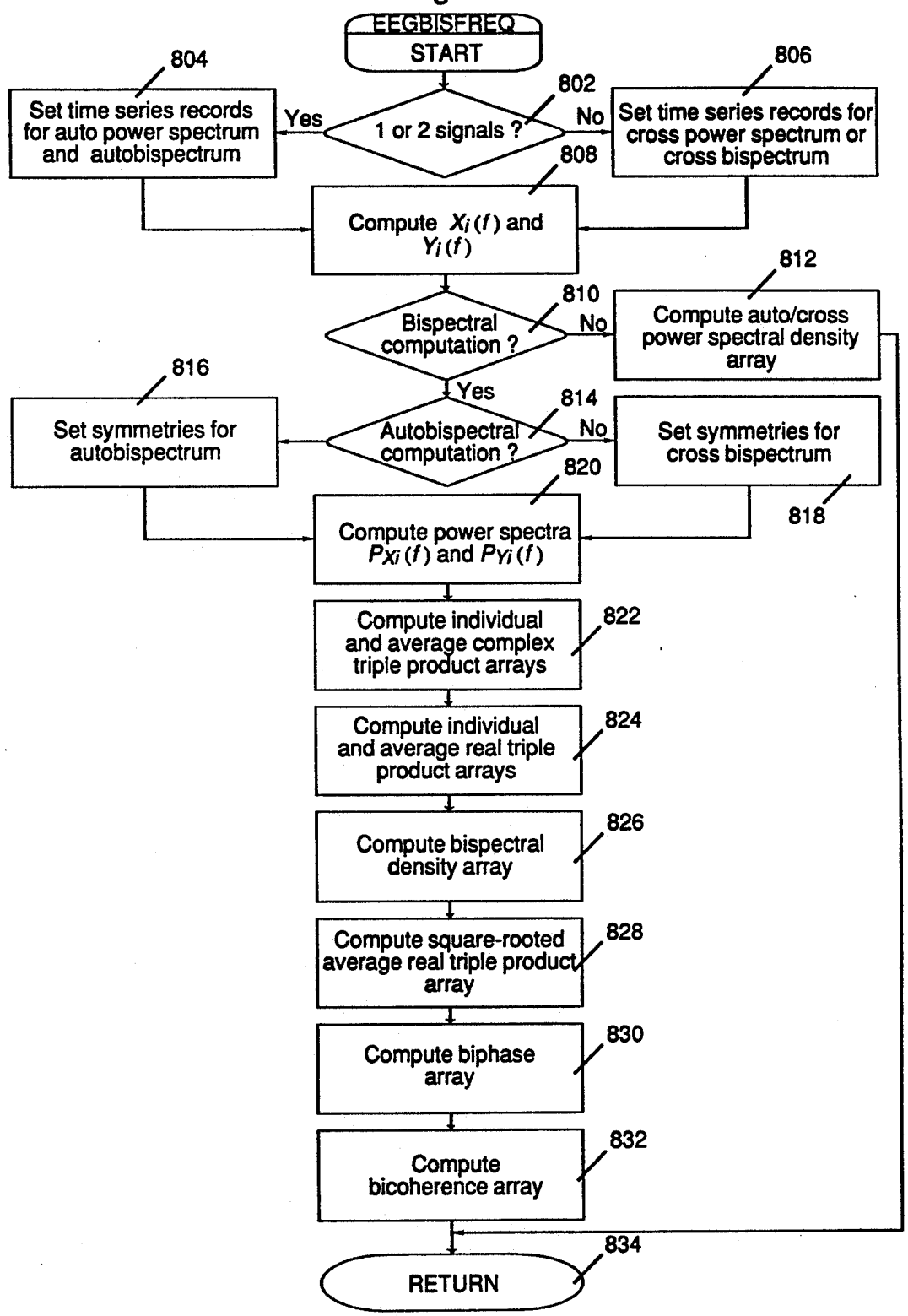

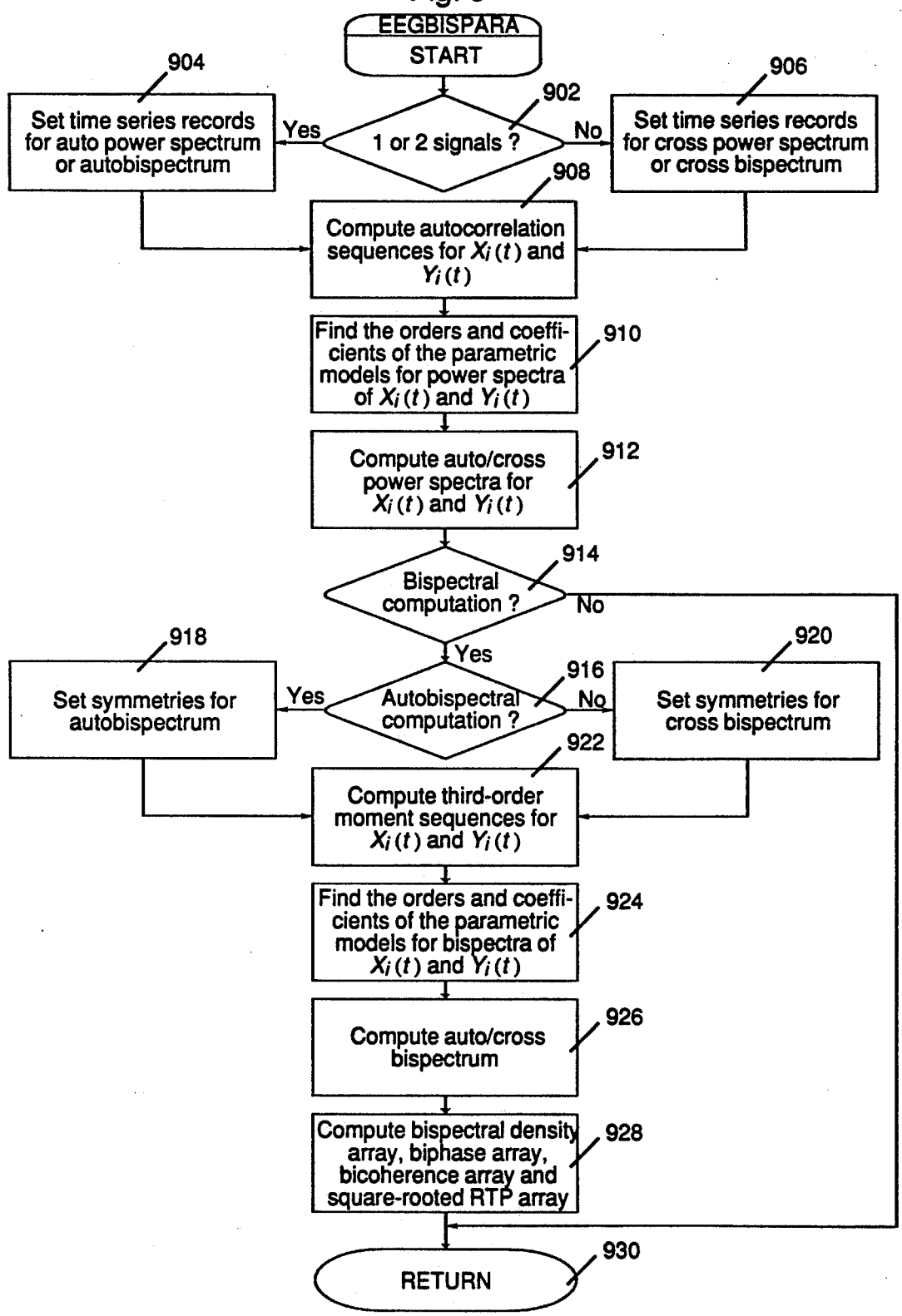

CEREBRAL BIOPOTENTIAL ANALYSIS SYSTEM AND METHOD

BACKGROUND Of THE INVENTION

The present invention relates to a real-time, high-resolution cerebral biopotential analysis system and method, and more particularly to a computer-based biopotential diagnostic system and method for quantitatively determining, in a noninvasive manner, cerebral phenomena that can be ascertained by analyzing the properties of cerebral electrical activity.

Despite a considerable expenditure of time and effort, current approaches to the quantitative, noninvasive assessment of cerebral electrical activity, as displayed in an electroencephalographic (EEG) waveform, have not been successful in fully extracting all of the information which is present in this complex waveform. A great need remains for an accurate, sensitive, reliable, and practical neurological profiling technology. In particular, contemporary intraoperative EEG monitoring techniques have not been widely adopted due to their inherent limitations. Indeed, large numbers of medical malpractice suits are believed to be related to post-anesthesia morbidity and mortality, and if such EEG monitoring techniques were reliable they certainly would have been adopted.

A number of devices known in the prior art are capable of tracking cerebral activity qualitatively. Techniques involving the use of the classical conventional analog EEG are restricted to analyses in the time domain, and require considerable training for adequate interpretation. Moreover, since the resolution of the human eye at standard EEG tracing speeds is limited, much of the fine structure of the EEG is invisible. Thus, visual EEG assessment is better characterized as an art rather than a science.

The use of frequency (power spectrum) analysis of the EEG in the 1960s introduced the notion of some basic processing of the signal prior to visual inspection and led to the application of frequency analysis of the EEG to various cerebral monitoring problems. In the past 25 years, over 100 papers have been published in the medical literature describing applications of power spectral analysis for purposes such as assessing the depth of anesthesia and cerebral ischemia under various intraoperative conditions. U.S. Pat. No. 4,557,270 issued to John also describes the use of power spectrum analysis to evaluate cerebral perfusion during open heart surgery. Several recent studies, however, have shown many deficiencies in the use of power spectral analysis to monitor cerebral perfusion and to determine postoperative neurological outcome. In addition, neither power spectrum analysis nor any other monitoring technique has been shown to be reliable, demonstrated by the fact that the Harvard Medical School Anesthesia Monitoring Standard does not include any type of intraoperative neurological monitoring, due, in all likelihood, to the complexity of interpreting raw EEG data and the unreliability of existing automated systems utilizing power spectrum or time-domain analytic techniques.

The discharge of thousands of bioelectrically active cells in the brain, organized in larger, interacting neural centers contributes to the formation of an electrical signal with a wide frequency spectrum that is rich in harmonics and extremely complex dynamics. Embedded in that signal is information regarding frequency content, nonlinearities, and phase relationships arising from the complex neuronal firing patterns that take place. Such firing patterns change constantly making the statistical properties of the EEG signal highly non-stationary. Because of the complexity of the EEG signal, conventional time and frequency modes of analysis have not been able to fully profile its behavior. This may be one of the reasons for the limited success of such approaches.

In the Fourier transform of the second order autocorrelation function (the power spectrum), processes are represented as a linear summation of statistically-uncorrelated sine-shaped wave components. Contemporary approaches to monitoring the EEG by means of the power spectrum have thus suppressed information regarding nonlinearities and inter-frequency phase relationships and are of limited utility in representing the EEG's dynamic structure.

Because the EEG is highly dynamic and nonlinear, the phase relationships within the EEG are the elements most likely to carry diagnostic information regarding cerebral function. The Fourier transform of the third order autocorrelation function, or autobispectrum, is an analytic process that quantifies deviation from normality, quadratic nonlinearities and inter-frequency phase relationships within a signal. The Fourier transform of the third order cross correlation function, or cross bispectrum, is an analytic process that provides similar information for two signals. We can generalize these techniques by defining the Fourier transform of the nth-order auto/cross correlation function, or the $n-1$ order auto/cross spectrum, as an analytic process that contains information regarding deviation from normality, as well as $n-1$ order nonlinearities and inter-frequency phase relationships in a signal. Auto/cross spectra beyond the bispectrum will be referred to as higher-order spectra.

Autobispectrum analysis techniques have been applied to the EEG signal to demonstrate the basic bispectral properties of the conventional EEG. Such studies have also been conducted to search for differences between the waking and sleeping states. Autobispectrum analysis and power spectrum analysis have also been used in an attempt to show that the EEGs of monozygotic twins are similar in structure. U.S. Pat. Nos. 4,907,597 and 5,010,891 issued to Chamoun describe the use of auto/cross bispectrum analysis of the EEG to evaluate cerebral phenomena such as quantifying depth and adequacy of anesthesia, pain responses induced by surgical stress, cerebral ischemia, consciousness, degrees of intoxication, ongoing cognitive processes and inter-hemispheric dynamic phase relations.

To date, no one has used auto higher-order spectrum or cross higher-order spectrum analysis for neurological diagnoses or monitoring of the cerebral phenomena described above.

A common problem in analyzing the data generated by any of the spectral techniques discussed above is the fact that the EEG's frequency distribution may dramatically change under relatively stable physiological conditions. Such changes will lead to changes in the power spectrum, bispectrum, and higher order spectra at the corresponding frequencies. For example, when hypnotic anesthetic agents are administered in low to medium concentrations, there is a substantial increase in the EEG activity in the 12-18 Hz frequency band. High doses of the same agents will lead to a sudden reduction in activity in the 12-18 Hz band and increase in activity in the 0.5-3.5 Hz band, followed by burst suppression at extremely high concentrations. A frequency-based analysis that uses the 12-18 Hz frequency band to track the patient's anesthetic depth during the administration of a hypnotic agent will provide a misleading assessment of the patient's depth when the shift in activity from high to low frequency occurs. Such transitions are even more complicated when a mixture of anesthetic agents is used.

Therefore, a principal object of the present invention is to provide a noninvasive high resolution electroencephalographic system and method capable of recognizing and monitoring physical phenomena that are reflected in properties of cerebral electrical activity.

Another object of the present invention is to provide a noninvasive electroencephalographic system and method capable of determining and monitoring depth and adequacy of anesthesia, pain responses during surgical stress, cerebral ischemia, cerebral hypoxia, levels of consciousness, degrees of intoxication, altered evoked potential responses, and normal or abnormal cognitive processes including but not limited to identifying patients with Alzheimer's disease and HIV-related dementias.

SUMMARY OF THE INVENTION

Accordingly, the system and method of the present invention uses a suitable electrode and amplifier system to obtain 19 unipolar EEG signals from regions of interest on both the left and right hemispheres of a subject's brain. The system uses high-gain low-noise amplifiers to maximize the dynamic range for low energy wave components of the signals. Band-pass filtering is used to reduce noise and to avoid aliasing. The system applies commonly used digital signal processing (DSP) techniques to digitize, to low pass filter (50 Hz), and to decimate the signals. Power spectral, bispectral, and higher-order spectral processing is then performed. In a preferred embodiment, the system divides the most recent 63 seconds of digitized EEG data from each lead into 60 4-second intervals, each with 3 seconds of overlap with the previous interval. For a selected set of derived leads, the system produces auto power spectrum, autobispectrum, and auto higher-order spectrum variables, by using either a Fast Fourier Transform (FFT) based approach or a parametric cubic fitting approach. Any pair of leads can be combined to compute cross power spectrum, cross bispectrum, and cross higher-order spectrum variables.

The outcome of the auto power spectral processing is a one-dimensional array that represents the power at each frequency within an EEG waveform from a single lead. Similarly, the cross power spectral processing will yield a one dimensional array representing the product of the energy at each of the frequencies in two waveforms. The outcome of the autobispectral and auto higher-order spectral processing is a set of arrays representing the dynamic power and phase coupling between all the possible combinations of frequencies within a waveform. Cross bispectral and cross higher-order spectral processing yields a set of arrays representing the dynamic power and phase coupling between all the possible combinations of frequencies from two waveforms. For auto/cross bispectrum analysis, four types of arrays can be generated: auto/cross bicoherence, auto/cross bispectral density, auto/cross real triple product, and auto/cross biphase. The same type of arrays can be generated for auto/cross higher-order spectral processing.

The values of auto/cross power spectrum, auto/cross bispectrum, and auto/cross higher-order spectrum arrays change with different interventions or disease states. Therefore, these values are used to create a diagnostic criterion. The power spectrum, bispectrum, and higher-order spectrum arrays are used to create a clinically useful single-valued index. This index is expected to accurately portray the particular diagnostic determination in question. The system uses these indices as a diagnostic figure of merit for the assessment of depth and adequacy of anesthesia, pain responses during surgical stress, cerebral ischemia, cerebral hypoxia, levels of consciousness, degree of intoxication, altered evoked potential responses, and normal or abnormal cognitive processes including but not limited to Alzheimer's disease and HIV-related dementias. This approach makes it possible for any operator to meaningfully interpret the output of the diagnostic device.

In situations where continuous monitoring is required, indices can be continuously displayed on a video terminal, thereby enabling the operator to interactively evaluate regions of interest. For record-keeping purposes, index values and other pertinent variables can be sent to a hard copy output device or stored on a storage device.

These and other objects and features of the present invention are more fully explained by the following detailed description and figures.

BRIEF DESCRIPTION OF THE FIGURES

FIG. 8 is a flow chart of the frequency-domain-based method for producing autobispectrum, cross bispectrum, auto power spectrum, or cross power spectrum used by the system of FIG. 1;

FIG. 9 is a flow chart of the parametric based method for producing autobispectrum, cross bispectrum, auto power spectrum, or cross power spectrum in the system of FIG. 1;

DETAILED DESCRIPTION OF THE PREFERRED EMBODIMENTS

Figure 1:
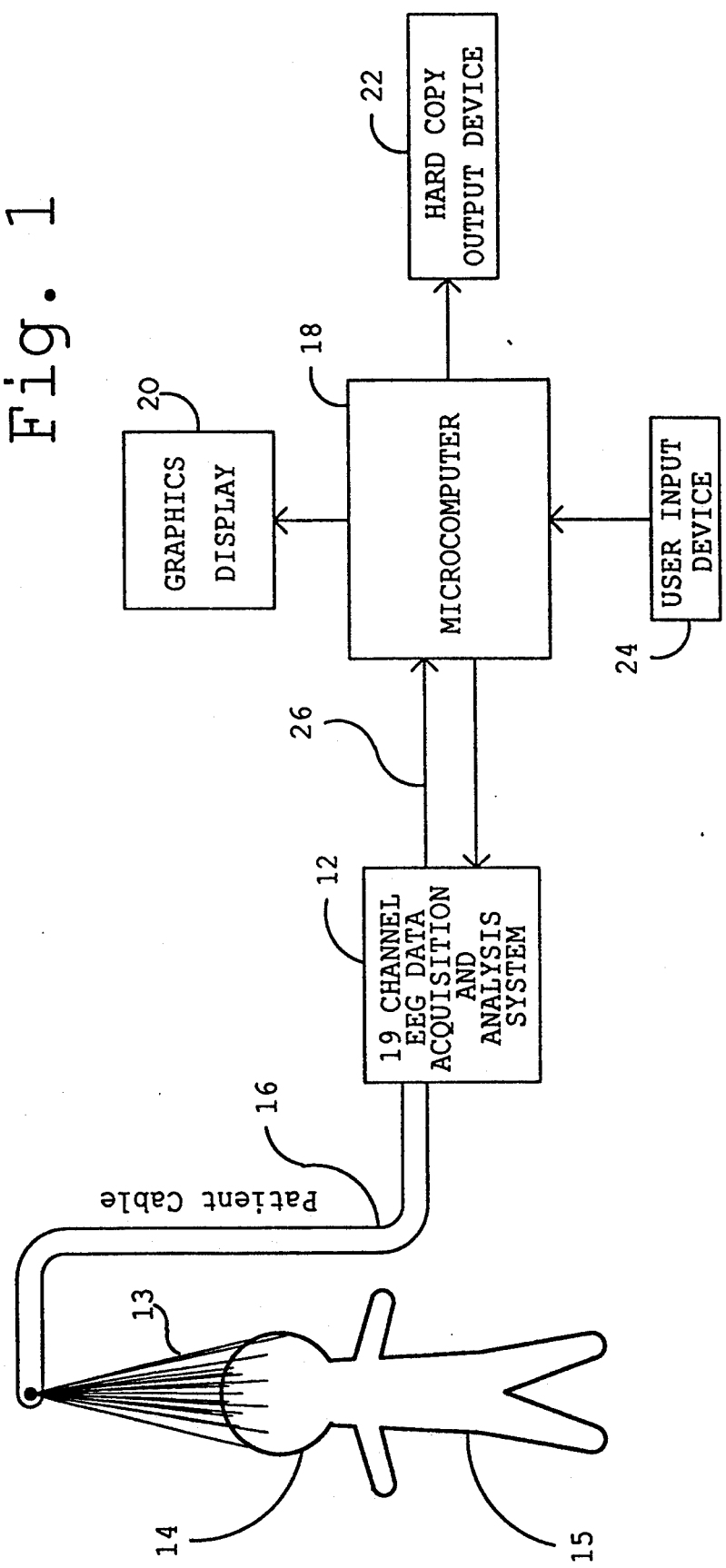
FIG. 1 is a schematic view of the system of the present invention for detecting cerebral phenomena in a non-invasive manner.

Referring to FIG. 1, the apparatus of the present invention includes a 19 channel EEG data acquisition and analysis system 12 connected to a microcomputer 18.

The EEG leads are connected to a patient's head 14 by a set of surface electrodes 13. The international 10/20 electrode system is preferred. The EEG signals are detected by the electrodes and transmitted over a patient cable 16 to the EEG data acquisition and analysis system 12.

The data acquisition and analysis system 12 filters and amplifies the EEG waveforms. Commonly used digital signal processing (DSP) techniques are applied to digitize, to low pass filter (50 Hz), and to decimate the signals. Power spectral, bispectral, and higher-order spectral processing can then be performed.

The system 12 generates all power spectrum, bispectrum, and higher-order spectrum arrays. These arrays are then used in conjunction with clinically predetermined coefficient arrays to produce diagnostic indices. These indices are sent to the host computer 18 and are displayed on the graphics display 20. Printed output of the diagnostic index is also available on the hard copy output device 22 which is connected to the microcomputer 18. The operator interacts with the acquisition and analysis components of the system by means of a user input device 24 with feedback on the graphics display 20.

Figure 2:
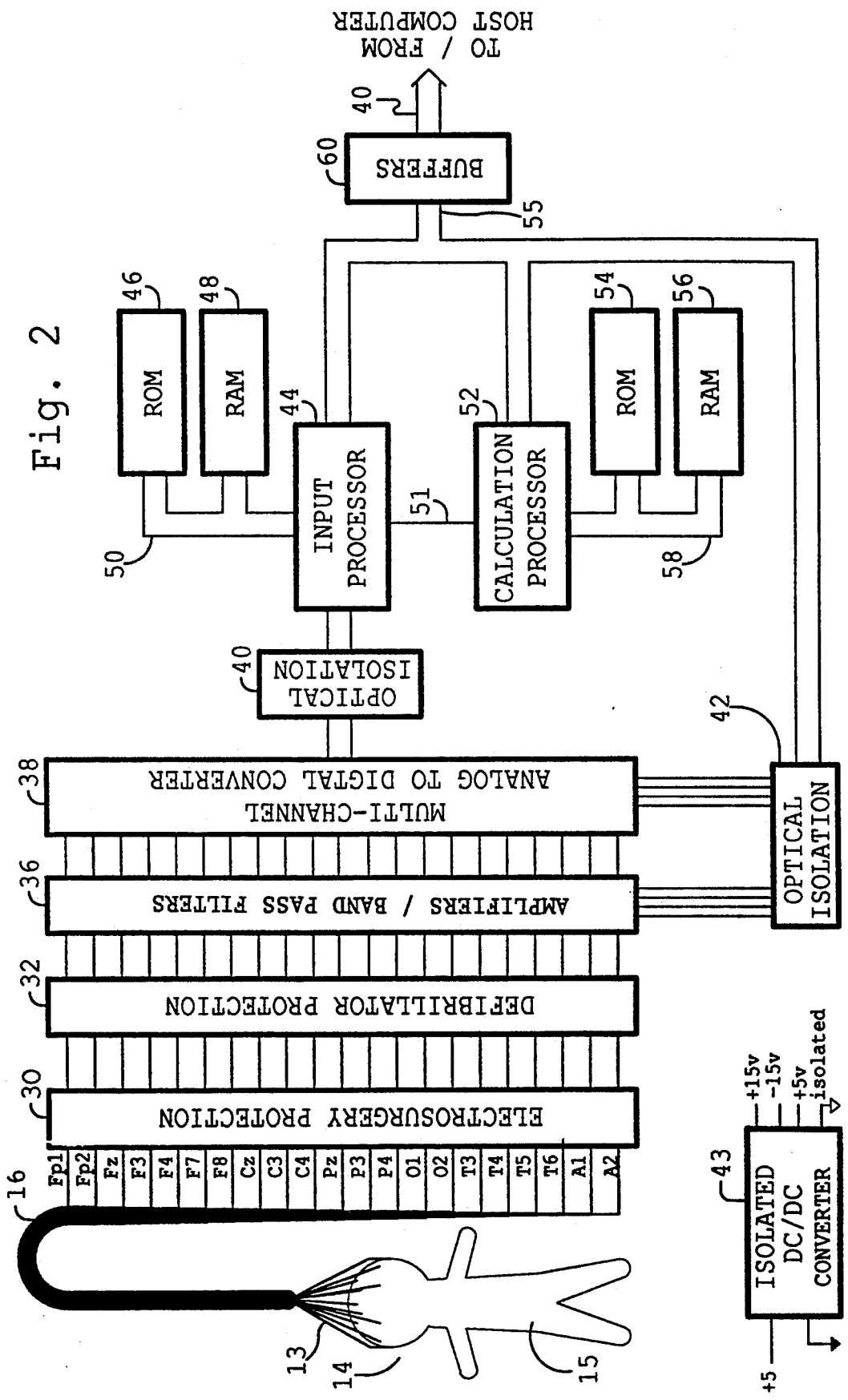
FIG. 2 is a schematic view of a 19 channel EEG data acquisition and analysis system utilized in the system of FIG. 1.

The 19 channel data acquisition and analysis system 12 is shown in greater detail in FIG. 2. The EEG surface potential, detected by surface electrodes 13 mounted on the patient's head 14, passes through an electrosurgery protection circuit 30, a defibrillator protection circuit 32, and an amplifier/filter circuit 36 before being passed on to the multi-channel analog to digital converter 38.

The electrosurgery protection circuit 30 includes a radio frequency (rf) filter, which limits the rf current through the patient leads 16 to less than 100 microamperes and thus protects the patient 15 from rf burns and protects the amplifiers 36 from damage resulting from exceeding the absolute maximum input voltage specified by the manufacturer. This circuit can be an LC circuit consisting of a generic inductor connected in series to a generic capacitor which is then connected to ground.

The defibrillator protection circuit 32 limits the voltage to the amplifiers 36 to a safe level when a defibrillator is applied to the patient 15 and discharged. This circuit can consist of a generic resistor connected, in series with the signal path, to a neon light bulb or other surge suppression device which is then connected to ground.

The amplifier/filter circuitry 36 is controlled by the microcomputer 18 for gain and filtering levels which may be adjusted by the operator. Preferred gain and filtering settings are discussed below. This circuit section consists of three stages. The first is a pre-amplifier stage that can be assembled using a wide variety of high-impedance pre-amplifiers such as those sold by National Semiconductor, Sunnyvale Calif. The second is a stage composed of programmable filters which will allow an adjustable band pass cutoff to be selected anywhere in the range of 0.1 Hz to 4 kHz. The filters can be designed using components from Frequency Devices, Haverhill Mass. The third stage is composed of programmable amplifiers which can be assembled from operational amplifiers used in conjunction with a multiplying digital to analog (D/A) converter. Both components can be obtained from National Semiconductor. The multiplying D/A is used to set the gain to the appropriate levels requested by the microcomputer 18.

The high impedance pre-amplifier of each channel will saturate to either the positive or negative supply voltage if the input of the pre-amplifier is not terminated. This will lead to large positive value or a large negative value at the output of amplifier/filter section 36. Such values will be used to identify lead failure.

The output of all 19 channels of the amplifier/filter 36 is fed to the multi-channel A/D converter 38 which is controlled by an input processor 44 for sampling rate settings. The analog signals are converted to digital data format suitable for input to the input processor 44. A/D converters sold by Analog Devices, Norwood MA can be used for this purpose.

The multi-channel A/D converter 38 is optically coupled to the input processor 44 by optical isolator 40. All control lines to the A/D convertor 38 are also optically isolated by optical isolator 42. Any optical isolator can be used for this purpose.

All DC power lines connected to the amplifiers 36 and A/D converter 38 are also isolated from the AC power line with a DC/DC convertor 43 in order to provide complete patient isolation from ground. DC/DC converters available from Burr Brown can be used for this purpose.

The basic instructions for controlling operation of the input processor 44 are stored in a read only memory (ROM) 46. The random access memory (RAM) 48 is used as a buffer memory for data and a portion of the RAM 50 can also be used as program memory when a control program is being downloaded from the microcomputer 18. The input processor 44 has a bus 50 to communicate with its RAM 48 and ROM 46 and a separate bus 55 for communicating with the microcomputer 18.

The memory architecture of the calculation processor is similar to that of the input processor. The basic instructions for controlling operation of the calculation processor 52 are stored in a read only memory (ROM) 54. The random access memory (RAM) 56 is used as a buffer memory for data and a portion of the RAM 56 can also be used as program memory when a control program is being downloaded from the microcomputer 18. The calculation processor 52 has a bus 58 to communicate with its RAM 56 and ROM 54 and uses the bus 55 for communicating with the microcomputer 18.

The A/D converter 38 acquires the data at high speed and filtering is done by the input processor 44 to exclude frequencies outside the region of interest. The input processor simultaneously decimates the sampling rate of the input data to a lower sampling rate. The input processor 44 transfers the filtered and decimated data stream to the microcomputer 18 for display of the raw input signals via the data bus 55 and buffers 60 to the microcomputer data bus 40. The input processor 44 also transfers the data to the calculation processor 52 for calculation of power spectrum and higher-order spectrum characteristics of the input signals via a serial communication interface 51. The calculation processor 52 calculates power spectrum and higher-order spectrum characteristics of the input data and produces diagnostic indices from the calculated power spectrum and higher-order spectrum data. The input processor can be any general purpose DSP processor such as the ADSP-2101 sold by Analog Devices, Norwood Mass. The calculation processor is a floating-point DSP processor in the preferred embodiment such as the TMS320C30 sold by Texas Instruments, Dallas, Tex.

Figure 3:
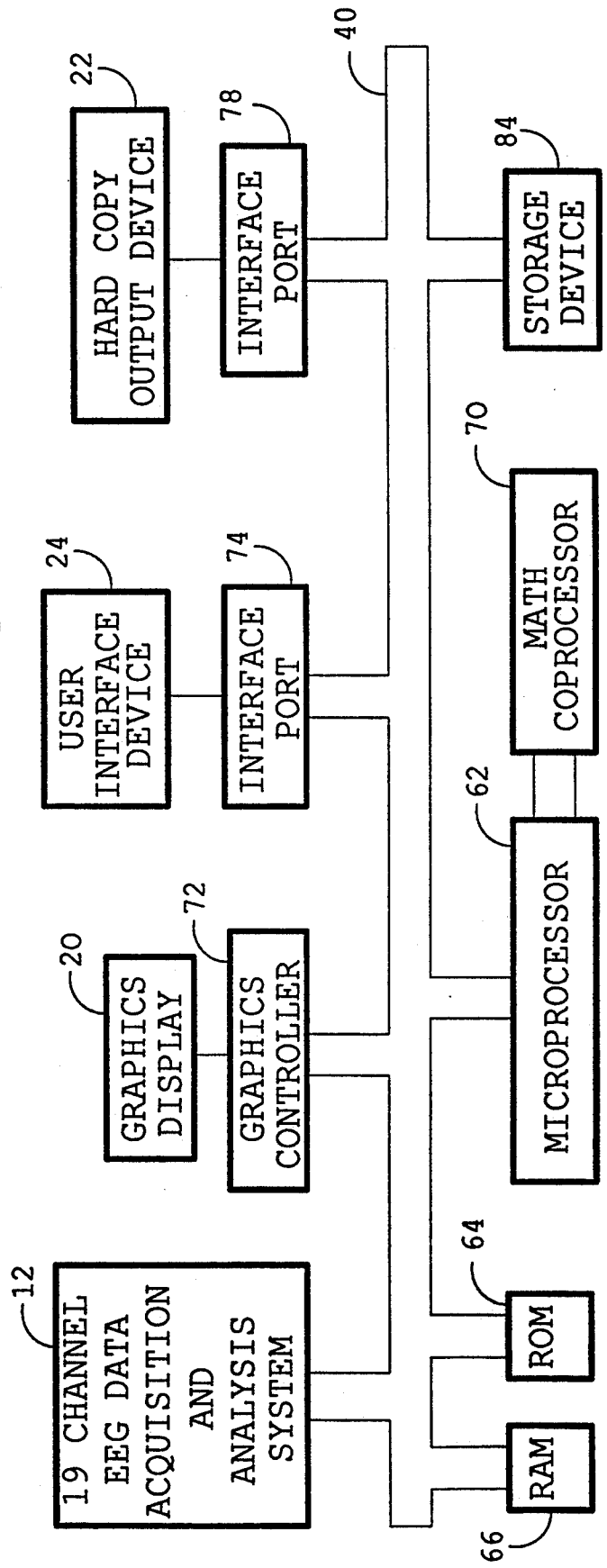
FIG. 3 is a schematic view of the microcomputer used to display the EEG power spectrum and bispectrum higher-order spectrum in the system of FIG. 1.

The host or microcomputer 18 of FIG. 1 is shown in greater detail in FIG. 3. The entire microcomputer system runs under control of a microprocessor 62 with the program memory stored in ROM 64. The RAM 66 is used for storage of intermediate data. The storage device 84 can be a Winchester disk or a large block of RAM or any other storage medium. It is used for storage of clinical information and can be used for archiving patient data.

In a preferred embodiment, the microcomputer 18 contains a math coprocessor 70 which is connected directly to microprocessor 62. The math coprocessor 70 is used for scalar and graphic calculations. A graphics controller 72 operating under program control of the microprocessor 62 drives a graphics display 20. An interface port 74 provides the connection from the microcomputer bus 40 to the user interface device 24. The user interface device 24 may be a keyboard, a pointing device or a keypad or any combination of these or similar devices. The interface port 74 can also provide a connection between the microcomputer and an external evoked potential stimulating device. This connection will allow the microcomputer to trigger a stimulus or easily identify the onset of an independently triggered stimulus.

Operator control of the entire acquisition, analysis and display procedure is controlled by the user interface device 24 with feedback on the graphics display 20. The data bus 40 can be used to send control data to the 19 channel data acquisition system 12 (e.g., filtering, gain, sampling rate, start/stop acquisition, perform self diagnostics) and to receive EEG data from the system, as well as to download program data to the system. A serial or parallel port 78 is provided to drive a hard copy output device 22 for printing desired diagnostic indices.

Figure 4:
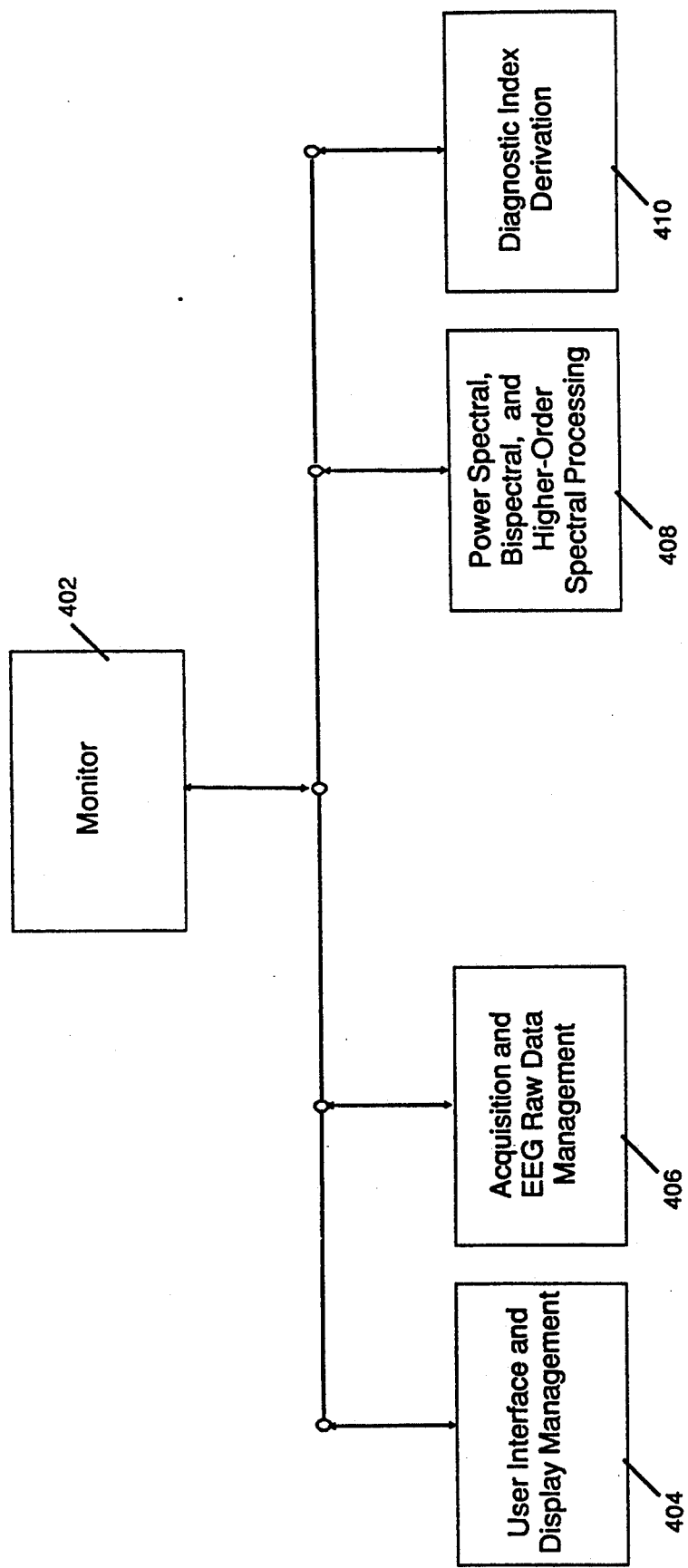
FIG. 4 is a schematic view of the processing operations performed by the system of FIG. 1.

Referring now to FIG. 4, a block diagram of the system operations and the method of the present invention is described. As mentioned above, the system and method of the present invention computes dynamic phase and density relations of EEG signals from a preselected number of leads. Single-valued diagnostic indices are then generated from the data arrays by using clinically predetermined coefficient arrays. The results are quantitative indices useful for analyzing cerebral electrical activity as it relates to, for example, the assessment of depth and adequacy of anesthesia, pain responses during surgical stress, cerebral ischemia, cerebral hypoxia, level of consciousness, degree of cerebral intoxication, altered evoked potential responses, and normal or abnormal cognitive processes that include but are not limited to Alzheimer's disease and HIV-related dementias.

The monitor module 402 handles the overall operations of the system via integration of data and process information from the user interface module 404, acquisition and raw EEG data management module 406, power spectral, bispectral and higher-order spectral processing module 408, and the diagnostic index derivation module 410. A detailed illustration of module 402 can be found in FIG. 5.

The operator controls and interacts with the system during the course of a procedure through the user interface and display management module 404. This interaction includes, but is not limited to, entry of information regarding the patient and type of diagnostic procedure underway; lead and acquisition settings; continuous display of acquisition status, lead integrity, and diagnostic indices corresponding to regions probed by each electrode; and requests for printing and archiving results to the storage device. Module 404 directly interacts with the monitor module 402. The operations handled by module 404 can be achieved under a commercially available environment such as Microsoft Windows.

The acquisition and raw EEG data management module 406, handles all of the raw EEG data checking and processing prior to power spectrum, bispectrum, and higher-order spectrum analysis. This includes, but is not-limited to, continuous acquisition of EEG data and the verification of its integrity; preparation of all unipolar EEG data for auto/cross power spectral, bispectral, and higher-order spectral processing. Module 406 directly interacts with the monitor module 402. A more detailed description of module 406 is provided below in connection with FIG. 7.

The power spectral, bispectral, and higher-order spectral processing module 408 controls the generation of all data arrays for power distribution, dynamic phase relations, and power coupling within the EEG. This information can be obtained by computing the auto/cross power spectrum, bispectrum, and higher-order spectra using either an FFT-based or parametric-based approach. The tasks performed by this module include, but are not limited to: Fourier transformation and the generation of power spectra; auto/cross bispectral density and higher order density generation; auto/cross bicoherence and higher order coherence generation; auto/cross bispectral real product and higher-order real product generation; and auto/cross biphase and higher-order phase generation. Module 408 directly interacts with the monitor module 402. A more detailed description of module 408 is provided below in connection with FIGS. 8 and 9.

The diagnostic index derivation module 410 generates the data values used in the diagnostic process. The task includes, but is not limited to, sorting the values in the frequency band of interest for each of the required power spectrum, bispectrum, or higher-order spectrum arrays; dividing each of the sorted arrays into bins representing portions of the distribution histogram of the sorted data (i.e. top 0–5%, top 5–10% as well as bottom 5%, etc.); summing the values in each bin to create a single number variable; creating a diagnostic index by multiplying the resultant sorted values from auto/cross power spectrum, bispectrum, and higher-order spectrum arrays by clinically predetermined coefficients; and summing all variables that have been multiplied by a coefficient to create a final univariate diagnostic index. Module 410 directly interacts with the monitor module 402. A more detailed description of module 410 is provided below in connection with FIG. 11.

Figure 5:
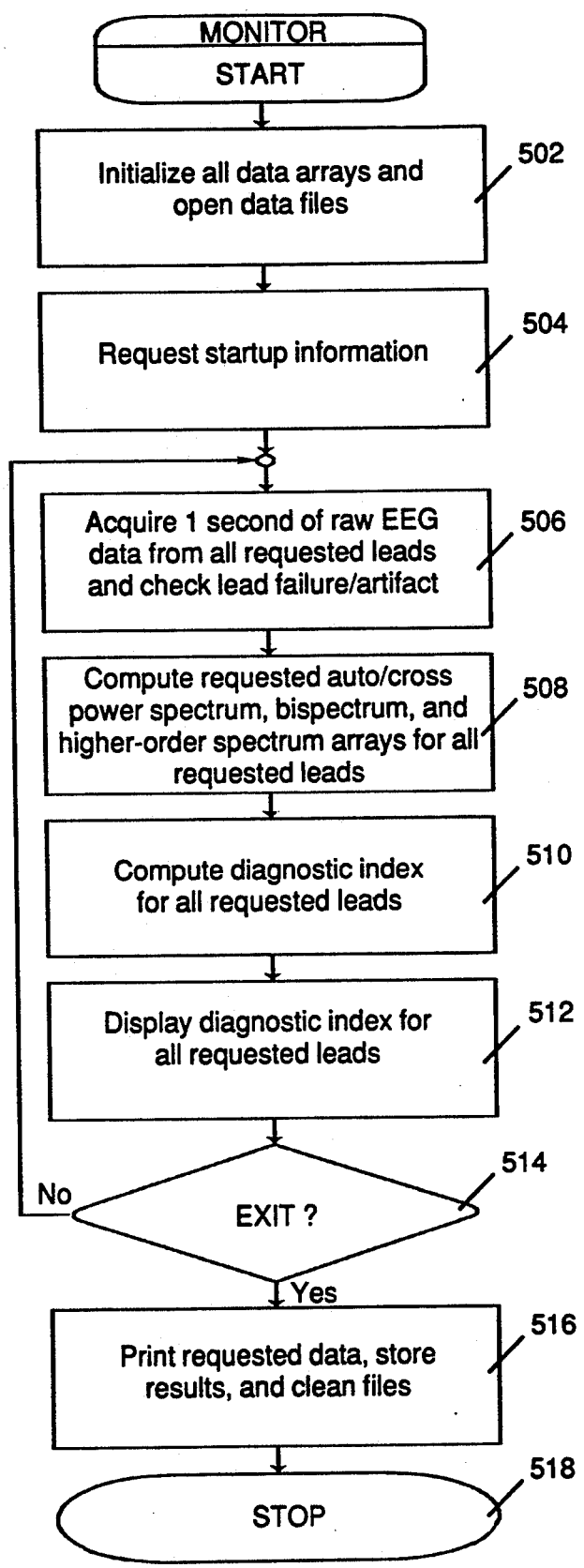
FIG. 5 is a flow chart of the operations of the monitor module shown in FIG. 4.

A schematic of the operation of the monitor module 402 is shown in FIG. 5. In initializing step 502, the data arrays are filled with the most recent 63 seconds of raw digitized EEG signals, and the power spectrum, bispectrum, and higher-order spectrum data for each lead are initialized to zero. The data files required for storage and files containing data bases required for the computation of diagnostic indices, are also opened in the initializing step 502.

In step 504 the system requests the information required to start the acquisition and diagnostic process from the user via the user interface module 404. This requested information includes patient descriptive statistics (sex, age, clinical symptoms, etc.), type of diagnostic procedure to be conducted, the leads used for auto power spectrum, bispectrum, and higher-order spectrum analysis as well as the leads to be used for cross power spectrum, bispectrum, and higher-order spectrum analysis.

In its default mode of operation the system continuously monitors the depth and adequacy of anesthesia and any pain responses during surgical stress using a default autobispectrum database. Default band pass filtering is performed, passing the range 0.5 to 50 Hz; the default sampling rate is set at 128 samples per second; and the default gain is set at 5000 for each lead. The following discussion and description of the preferred embodiments will emphasize autobispectral processing performed on EEGs from specific electrode sites that best provide depth of anesthesia information. Other modes of operation will be described more generally.

According to the international 10/20 electrode system, the 19 EEG signals that can be acquired using the system are: Fp1, Fp2, F7, F3, Fz, F4, F8, T3, C3, Cz, C4, T4, T5, P3, Pz, P4, T6, O1, and O2 (A1 or A2 for reference).

In order to perform auto power spectrum, bispectrum, and higher-order spectral analysis, one signal is required. This signal can be measured directly from any of the above electrodes or it can be synthesized by linearly combining signals from two or more EEG leads. For example, two analog signals can be subtracted from each other using a differential amplifier to yield a third signal. The same operation can be performed on the two digitized signals using numerical subtraction. The auto power spectrum data will provide information regarding the power distribution within the signal; the autobispectrum data will provide information regarding deviation from normality, quadratic nonlinearities and inter-frequency phase relationships within the signal; finally, auto higher-order spectrum data will provide information regarding deviation from normality, higher-order nonlinearities, and inter-frequency phase relationships within the signal. Such processing will determine if the signal is made up of independent wave components or whether certain frequencies are simply harmonics of nonlinearly interacting fundamentals. Cerebral phenomena that alter the nonlinear frequency structure of the signal at the location probed by the electrode are best quantified by autobispectrum and higher-order spectrum type approaches.

In order to perform cross power spectrum, bispectrum, and higher-order spectrum analysis, two signals are required. The two signals can be measured directly from any of the above electrodes or either of the two signals can be synthesized by linearly combining two or more of the EEG leads as described earlier. The cross power spectrum data will provide information regarding the power correlation between the two signals. The cross bispectrum data will provide information regarding deviation from normality, quadratic nonlinearities, and inter-frequency phase relationships between the two signals. Finally, cross higher-order spectrum data will provide information regarding deviation from normality, higher-order nonlinearities, and inter-frequency phase relationships between the two signals. Such processing will determine if the frequencies in signal "X" are independent or whether the are harmonics of fundamentals present in signal "Y". This provides a better characterization of the relationship between two signals originating from separate regions of the cortex. Cerebral phenomena that alter nonlinear frequency relations between the various regions of the cortex are best quantified by cross bispectrum and cross higher-order spectrum approaches.

Since the effects of anesthesia are reflected by more global changes in the EEG, the preferred embodiment will use six signals to illustrate the operation of the system using autobispectrum analysis for the monitoring of the depth of anesthesia. The six signals are derived from the following electrode placements: left and right frontal (FL/FR) signals are derived from (Fp1-Cz) and (Fp2-Cz) respectively; left and right parietal (PL/PR) signals are derived from (P3-Cz) and (P4-Cz) respectively; left and right fronto-parietal (FPL/FPR) signals are derived from (Fp1-P3) and (Fp2-P4) respectively.

In step 506, a new one-second buffer of raw EEG data is acquired. The system performs artifact detection on the new one-second buffer and properly updates all data arrays. Any transmission of artifactual data is displayed to the operator in order to invoke the operator into correcting the problem.

The system, in step 508, computes auto power spectrum and autobispectrum arrays for the signals FL, FR, PL, PR, FPL, FPR. Other signals may, of course, be used for auto/cross power spectral, bispectral, and higher-order spectral processing. Two different approaches for power spectrum, bispectrum, and higher-order spectrum computation will be discussed below with reference to FIGS. 8 and 9.

In step 510, the single-valued diagnostic indices from all generated auto/cross power spectrum, bispectrum, and higher-order spectrum arrays are computed. The clinically predetermined coefficient arrays for the auto/cross power spectrum, bispectrum, and higher-order spectrum arrays are used for the diagnostic index computations. The generation of the coefficient arrays is discussed later. The system instantaneously displays, in step 512, all computed diagnostic indices for all signals being analyzed. In step 514, the system checks for an exit request, and if such a request has not been made, the system repeats steps 508 through 514. In step 516, requested printouts are produced, results are stored to a storage device for archival purposes and all files are closed. In step 518, the process is terminated.

Figure 6B:
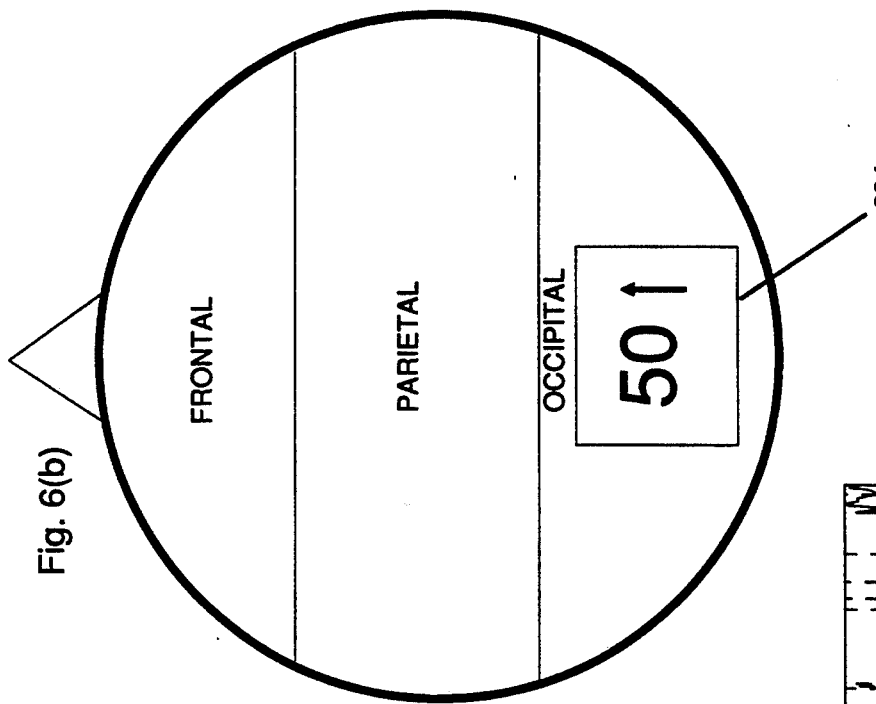
FIGS. 6(a)-6(c) are views of sample display representations of diagnostic index generated by the system of FIG. 1.
Figure 6A:
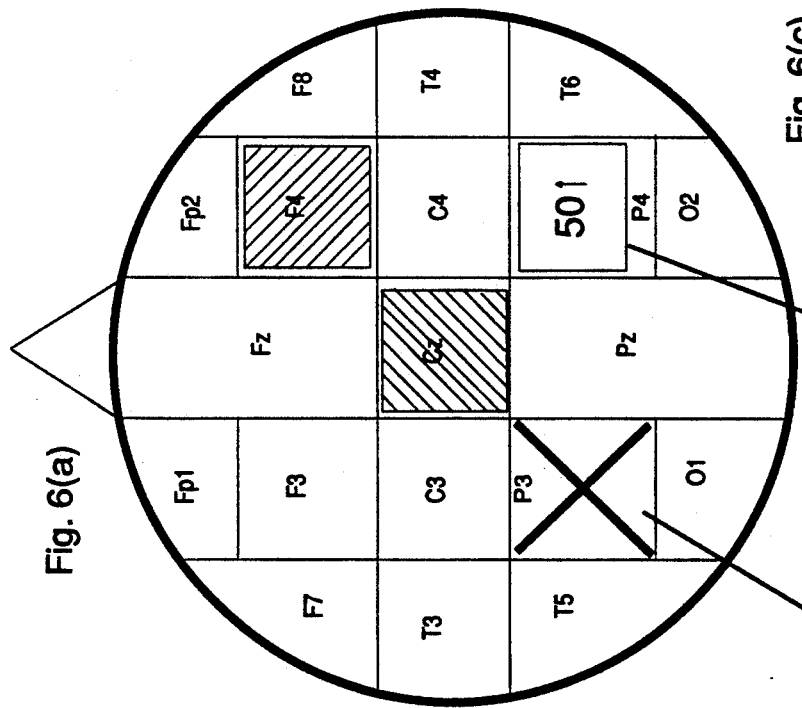
Figure 6C:
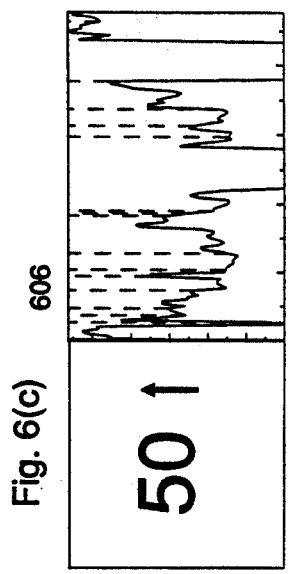

A sample condensed display representation generated by the system is shown in FIGS. 6(a)–6(c). Representations of the patient's head are shown on the graphics display in FIG. 6(a) and FIG. 6(b). The first illustration FIG. 6(a) is divided into nineteen sections each representing the region probed by an electrode. The second illustration FIG. 6(b) is divided into three horizontal sections representing combined left and right hemisphere activity probed by a group of electrodes in that region. The virtual head displayed on the screen may be partitioned as required for a particular diagnostic or monitoring application. For example, if a global effect like depth of anesthesia is being tracked, then one unified index along with its trend may occupy the whole display area.

For head representation FIG. 6(a), each section contains the instantaneous value of the index 602 using EEG data acquired from the electrode in that region. For head representation FIG. 6(b), each section contains the instantaneous value of the computed index 604 using EEG data acquired from several electrodes in that region. Next to each index value, a color-coded arrow is used to show the instantaneous change in the direction of the index. The arrow will be green if the index is within acceptable limits set as by the operator. The arrow will change to yellow if the index moves into a warning zone. A flashing red bar will replace the arrow if the index has a value that is outside the acceptable limits set for the patient.

At the request of the operator, the instantaneous value of the index and its trend for any section can be displayed as an enlarged view 606 for closer examination as shown in FIG. 6(c). This will facilitate the examination of the patient's status at a distance. Each section will be covered by a large "X" 608 if a lead fails or artifact was detected, for any of the leads contributing to the data required to generate the diagnostic index for that region.

Figure 7:
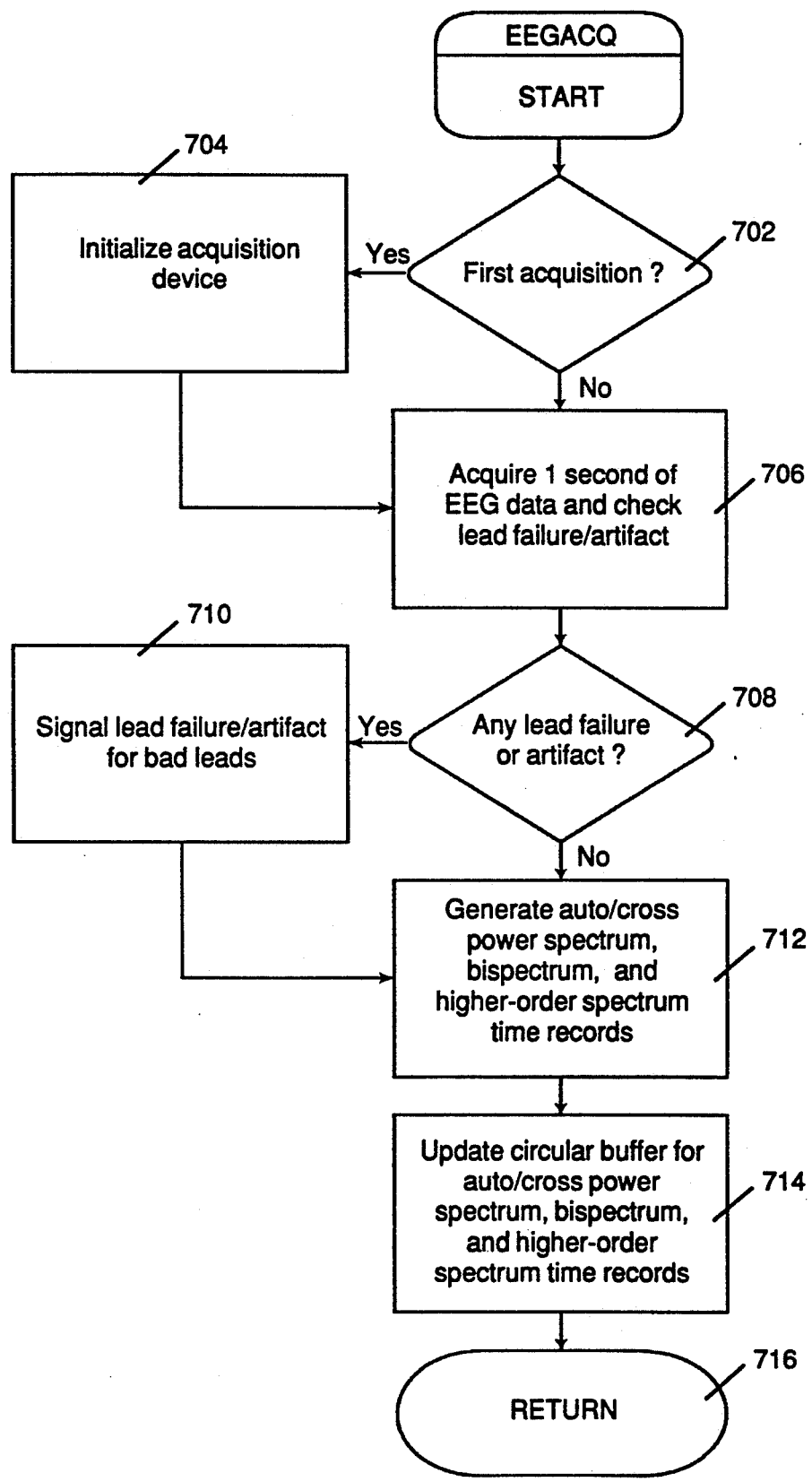
FIG. 7 is a flow chart of the operations of the acquisition and EEG raw data management module of the system shown in FIG. 4.

Referring to FIG. 7, the acquisition and raw EEG data management module 406 will now be described in greater detail. In step 702, the system checks whether new data is being acquired for the first time. If it is, the acquisition system 12 in step 704 is supplied with requested filtering, gain, sampling rate, and lead selection information. The default settings are band pass 0.5–50 Hz for filtering, 5000 for gain, 128 samples/sec for sampling rate and signals from the lead combinations FL, FR, PL, PR, FPL and FPR are acquired. The above settings are quite different when the system is analyzing evoked EEG responses rather than continuous EEG signals. Common gain and filter settings to acquire signals for the various EEG evoked potentials are described below.

EEG evoked potentials are a means by which the sensory areas of the brain and of the central nervous system may be assayed by detecting responses in the EEG to sensory stimuli. There are three common methods: Pattern-shift visual evoked potentials (PSVEP) involve a visual pattern that is shown to the patient and changed. For example, a strobe light may be flashed or a black and white checkerboard may be reversed (black for white and vice versa). Brainstem auditory evoked potentials (BAEP) uses a controlled auditory stimulus such as a click produced by a signal generator. Finally, somatosensory evoked potentials (SEP) employs either physiologic (touch or muscle stretch) or electrical stimuli. In all evoked potential methods, electrodes are placed near the appropriate centers of the brain (i.e. over the visual cortexes in the case of visual evoked potentials) and EEGs are recorded for a certain period of time beginning with the administration of the stimulus. The stimulus is repeated many times and the resulting recordings are averaged (traditionally, in the time domain) so as to eliminate all parts of the EEG signal except that due to the stimulus. In the present invention, a series of power spectrum, bispectrum, or higher-order spectrum arrays, as produced from the EEG of the evoked responses, is averaged.

For each evoked potential method, different filter and gain settings are used. For example, a range of common gain settings for pattern-shift visual evoked potentials is 20,000 to 100,000. A range of common filter settings for PSVEPs is 1 to 3 Hz for the low end of the band pass and 100 Hz to 300 Hz for the high end. The methods and use of evoked potentials are described more fully in Evoked Potentials In Clinical Medicine, by Chiappa 1983, the teachings of which are incorporated herein by reference.

In step 706, the acquisition system 12 acquires one second's worth of new data for all requested leads. Or the signal from one complete evoked potential response is acquired if the system is analyzing evoked potentials. The system detects lead failures during the acquisition cycle in step 708 by checking for very large positive or negative values. Also in step 708, publicly available algorithms are used to check for artifacts in each lead. In step 710, leads that have failed and those producing artifactual data are marked for the monitor module 402.

In step 712, the most recent 4-second record for each of the signals is assigned to $X_i(t)$, where $X_i(t)$ is the individual time series records provided for auto power spectral, autobispectral, and auto higher-order spectral processing (herein, the time series $X_i(t)$ (for all t, for one specific i) is referred to as a record). In situations where cross power spectral, bispectral, and higher-order spectral processing is required, the most recent 4-second record from the second signal is assigned to $Y_i(t)$. In the preferred embodiment, $Y_i(t)$ is set to equal $X_i(t)$ in all cases, since only auto power spectrum, auto bispectrum, and auto higher-order spectrum computations are to be performed. The index i denotes the record number from 1 to 60. If evoked potentials are being analyzed the most recent, complete, evoked potential response from each signal is assigned to the appropriate $X_i(t)$ and $Y_i(t)$ as described above. Using evoked potential responses as individual records will allow us to average a large number of them in the power spectrum, bispectrum, and higher-order spectrum domains.

In step 714, a circular buffer mechanism is used for storing the raw EEG for each lead, as well as the auto-/cross power spectrum, bispectrum, and higher-order spectrum arrays for the sixty most recent 4-second $X_i(t)$ and $Y_i(t)$ records for each lead. The buffer is updated by storing the most recently acquired and processed data in the location of the oldest data. Operation of the system returns to the monitor module 402 in step 716.

Referring now to FIG. 8, the frequency-domain-based procedures for producing the auto power spectrum, autobispectrum, cross power spectrum, or the cross bispectrum will now be discussed. In step 802, the system checks whether the computation to be performed requires one signal or two signals. Typically, one time series is required to perform autospectrum analysis and two time series are required to perform cross spectrum analysis.

In step 804, the system sets time records in the following manner in order to proceed with auto power spectral or autobispectral computation of the unipolar lead. As these computations require only one signal, the second set of records ($Y_i(t)$) is set to equal the first set ($X_i(t)$). As a consequence, the corresponding Fourier transforms of $X_i(t)$ and $Y_i(t)$, respectively $X_i(f)$ and $Y_i(t)$, are also equal:

$$X_i(t) = Y_i(t) \rightarrow X_i(f) = Y_i(f)$$

where i denotes the record number which, in this embodiment, ranges from 1 to 60.

In step 806, time records are set for cross power spectral and cross bispectral analysis using two separate time series signals. As a consequence, the corresponding Fourier transforms are not equal:

$$X_i(t) \neq Y_i(t) \rightarrow X_i(f) \neq Y_i(f)$$

where $X_i(t)$ and $Y_i(t)$ represent individually derived time series records from two separate regions probed by two or more electrodes.

The fast Fourier transform (FFT) $X_i(f)$ and $Y_i(f)$ of each of the 60 selected records for that signal, is computed using a standard IEEE library routine (or any other publicly available routine) in step 808. If requested, the series of transformed records, $X_i(f)$ and $Y_i(f)$, may be each normalized by dividing the value at each frequency by the constants $C_{xi}$ and $C_{yi}$, respectively. These constants are derived separately for each record and each series (either X or Y). The constant could be the total power, the largest peak in the spectrum of interest, or some other derivative of $X_i(f)$, $X_i(t)$, $Y_i(f)$, and $Y_i(t)$.

In step 810, the system checks whether the computation to be performed is a power spectrum or bispectrum computation.

The system computes the auto/cross power spectral density values (PD(f)) in step 812 by using the following equations where PC(f) is the average complex product for a signal or signal pair:

$$PC(f) = \frac{1}{N} \sum_{i=1}^{N} X_i(f) \cdot Y^*_i(f)$$

$$PD(f) = |PC(f)|$$

where $Y_i^*(f)$ is the complex conjugate of $Y_i(f)$ ($0 < f < N/2$) and N is the number of records (60 in the preferred embodiment). The system then returns the requested auto/cross power spectral density array to monitor module 402.

If the system is performing a bispectral computation in step 814, the system checks whether the computation to be performed is an autobispectrum or cross bispectrum computation.

Autobispectrum analysis is a special case of crossbispectrum analysis and therefore different rules of symmetry apply. In step 816, the system uses the following equations to determine what ranges of $f_1$ and $f_2$ to use during autobispectral computation:

$$f_1 + f_2 < N/2$$

where N equals the number of samples per record (512=4 secs per record * 128 samples per sec in a preferred embodiment), and $$0 < f_2 < f_1$$

where $f_1$ and $f_2$ (also referred to as $F_1$ and $F_2$ or Frequency 1 and Frequency 2) denote the frequency pairs over which bispectrum computation will be carried out.

In step 818, the following equations are used to determine the range of $f_1$ and $f_2$ for cross bispectrum analysis:

$$f_1 + f_2 < N/2$$

$$0 < f_1 < N/2$$

$$0 < f_2 < N/2$$

$$-2f_2 < f_1$$

where all variables represent the same values as they do for autobispectral analysis, except that for crossbispectral analysis $X_i(f)$ and $Y_i(f)$ represent the Fourier transform of the individually derived time series records from two separate regions.

In Step 820, the power spectra $P_{xi}(f)$ and $P_{yi}(f)$ of each of the 60 selected records for that signal are computed by squaring the magnitudes of each element of the Fourier transform $X_i(f)$ and $Y_i(f)$ respectively.

The system computes the average complex triple product in step 822 by using the following equations where $bc_i(f_1, f_2)$ is an individual complex triple product from one 4-second record and $BC(f_1, f_2)$ is the average complex triple product for all 60 records:

$$bc_i(f_1, f_2) = X_i(f_1) \cdot X_i(f_2) \cdot Y^*_i(f_1 + f_2)$$

where $Y_i^*(f_1 + f_2)$ is the complex conjugate of $Y_i(f_1 + f_2)$, and $$BC(f_1, f_2) = \frac{1}{N} \sum_{i=1}^{N} bc_i(f_1, f_2)$$

where N is the number of records (60 in the preferred embodiment)

The average real triple product is computed in step 824 by using the following equations where $br_i(f_1, f_2)$ is an individual real triple product from one 4-second record and $BR(f_1, f_2)$ is the average real triple product for all 60 records:

$$br_i(f_1, f_2) = P_{xi}(f_1) \cdot P_{xi}(f_2) \cdot P_{yi}(f_1 + f_2)$$

$$BR(f_1, f_2) = \frac{1}{N} \sum_{i=1}^{N} br_i(f_1, f_2)$$

where N is the number of records (60 in the preferred embodiment) In step 826, the array of auto/cross bispectral density values (BD ($f_1$, $f_2$)) are computed using the following equation:

$$BD(f_1, f_2) = |BC(f_1, f_2)|$$

In step 828, the array of the square roots of the average real triple products (SBR($f_1$, $f_2$)) are computed using the following equation:

$$SBR(f_1, f_2) = [BR(f_1, f_2)]^{\frac{1}{2}}$$

In step 830, the system computes the array of auto/cross values ($\phi(f_1, f_2)$) using the following equation:

$$\phi(f_1, f_2) = \tan^{-1}[Im(BC(f_1, f_2))/Re(BC(f_1, f_2))]$$

$$0 < \phi < 2\pi \text{ (radians)}$$

In step 832, the system computes the array of auto/cross bicoherence values (R($f_1,f_2$)) using the following equation:

$$R(f_1, f_2) = BD(f_1, f_2)/SBR(f_1, f_2)$$

$$0 < R < 1$$

In step 834, the system returns the requested auto/cross power spectral density array or auto/cross bispectral density, squared-rooted average real triple product, bicoherence, biphase arrays to the monitor module 402.

The above frequency-domain-based equations used to compute the auto/cross bispectrum arrays can be generalized to compute auto/cross higher-order spectral arrays. This will allow the computation of the trispectrum, quadspectrum, etc. Assuming that the arrays for a Kth-order spectrum are to be computed the following equations can be used:

The average complex Kth order product:

$$KC(f_1, f_2, \ldots, f_{K-1}) = \frac{1}{N} \sum_{i=1}^{N} X_i(f_1) \cdot X_i(f_2) \cdot \ldots$$

$$\cdot X_i(f_{K-1}) \cdot Y^*_i(f_1 + f_2 + \ldots + f_{K-1})$$

where N is the number of records (60 in the preferred embodiment)

The average real Kth-order product:

$$KR(f_1, f_2, \ldots, f_{K-1}) = \frac{1}{N} \sum_{i=1}^{N} P_{xi}(f_1) \cdot P_{xi}(f_2) \cdot \ldots$$

$$\cdot P_{xi}(f_{K-1}) \cdot P_{yi}(f_1 + f_2 + \ldots + f_{K-1})$$

The auto/cross Kth-order spectral density:

$$KD(f_1, f_2, \ldots, f_{K-1}) = |KC(f_1, f_2, \ldots, f_{K-1})|$$

The auto/cross Kth-order coherence:

$$R(f_1, f_2, \ldots, f_{K-1}) = KD(f_1, f_2, \ldots, f_{K-1})/[KR(f_1, f_2, \ldots, f_{K-1})]^{\frac{1}{2}}$$

$$0 < R < 1$$

The auto/cross Kth-order phase:

$$ti\ \phi(f_1, f_2, \ldots, f_{K-1}) = \tan^{-1}[Im(KC(f_1, f_2, \ldots, f_{K-1}))/Re(KC(f_1, f_2, \ldots, f_{K-1}))]$$

$$0 < \phi < 2\pi \text{ (radians)}$$

FIG. 9 illustrates a parametric-based method for producing the auto power spectrum, autobispectrum, cross power spectrum, or cross bispectrum. In steps 902, 904, and 906 the system sets the time series records in the same manner as described above in steps 802, 804, and 806 respectively. The auto/cross power spectra of $X_i(t)$ and $Y_i(t)$ are estimated in steps 908, 910, and 912. This estimation method includes two major stages, the autoregressive (AR) model order selection and the auto-/cross power spectrum computation for $X_i(t)$ and $Y_i(t)$. In step 908, the system computes two sequences of autocorrelations, $\{R_{2X}(m)\}$ and $\{R_{2Y}(m)\}$ using the following equation.

$$R_{2z}(m) = \frac{1}{M \cdot N} \sum_{i=1}^{M} \sum_{t=0}^{N-|m|} z_i(t) z_i(t+m),$$

$$z = X \text{ or } Y, \text{ and } m = 0, 1, \ldots, L$$

where M is the number of records of each signal (60 in the described embodiment), and N is the number of samples per record (512 in the described embodiment), and L is greater than the largest possible AR filter order (50 in the described embodiment).

The Final Prediction Errors, $FPE_X(m)$ and $FPE_Y(m)$ are calculated for all orders, $m = 1, 2, \ldots, L$, by performing a Levinson recursion function on each autocorrelation sequence in step 910 in order to find the order of the AR filter. The order of the AR filters can be determined by finding the location of the minimum of Final Prediction Errors: $FPE_X(m)$ and $FPE_Y(m)$ respectively, i.e., $$FPE_X(Q_X) = \min\{FPE_X(m)\} \text{ and}$$
$$FPE_Y(Q_Y) = \min\{FPE_Y(m)\}$$

where $Q_X$ and $Q_Y$ are the locations of the minimum values for $FPE_X(m)$ and $FPE_Y(m)$ (respectively) and, consequently, the orders of the AR filters of the power spectra $X_i(t)$ and $Y_i(t)$ (respectively).

Once the orders of the AR filters for auto power spectra are known, the autocorrelation sequences, $\{R_{2X}(m)\}$ and $\{R_{2Y}(m)\}$, are entered into a Levinson recursion with order $Q_X$ and $Q_Y$, respectively, instead of L. The coefficients, $\{c_{iX}, i = 0, 1, \ldots, Q_X\}$ and $\{c_{iY}, i = 0, 1, \ldots, Q_Y\}$, obtained from the recursion are the coefficients of the AR filters for auto power spectra of $X_i(t)$ and $Y_i(t)$ respectively. Then, in step 912, the transfer function of the AR filters for auto power spectra of $X_i(t)$ and $Y_i(t)$ are computed as the square root of the prediction error ($\sigma_z$) divided by the Fourier transform of the coefficients, i.e., $$H_{PZ}(f) = \frac{\sigma_z}{1 + \sum_{i=1}^{Q_z} c_{iz} e^{-j2\pi f i}}, z = X, Y.$$

The auto/cross power spectral density values (PD(f)) is the magnitude of the complex product of $H_{PX}(f)$ and the complex conjugate of $H_{PY}(f)$, i.e., $$PC(f) = H_{PX}(f) \cdot H_{PY}^*(f)$$

$$PD(f) = |PC(f)|$$

If requested, the same normalization used in step 808 is may be used here (on $H_{PZ}(f)$).

In step 914, the system checks whether the computation to be performed is a bispectrum computation, and if it is not, the system returns the requested auto/cross power spectral density array to monitor module 402.

In steps 916, 918, and 920, the system sets the symmetries in the same manner as described above in steps 814, 816, and 818.

The system estimates the auto/cross bispectrum in steps 922, 924, and 926. The estimation process includes two major stages: the order selection and bispectrum computation. In step 922, two sequences of third-order moments, $\{R_{3X}(\tau)\}$ and $\{R_{3Y}(\tau)\}$ are computed using the following equation.

$$R_{3z}(\tau) = \frac{1}{M \cdot N} \sum_{i=1}^{M} \sum_{t=s_1}^{s_2} z_i(t) z_i^2(t+\tau),$$

$$z = X, Y, \text{ and } \tau = -L, \ldots, L$$

where $s_1 = \max(1, 1-\tau)$, $s_2 = \min(N, N-\tau)$, and L is greater than the largest possible AR filter order (e.g. 50).

In step 924, two matrices $T_X$ and $T_Y$ are formed as follows.

$$T_z = \begin{pmatrix} R_{3z}(-L) & R_{3z}(-L+1) & \ldots & R_{3z}(0) \\ R_{3z}(-L-1) & R_{3z}(-L) & \ldots & R_{3z}(-1) \\ \cdot & \cdot & \ldots & \cdot \\ \cdot & \cdot & \ldots & \cdot \\ \cdot & \cdot & \ldots & \cdot \\ R_{3z}(-2L) & R_{3z}(-2L+1) & \ldots & R_{3z}(-L) \end{pmatrix},$$

$z = X, Y.$

From the assumption we made about the AR filter of bispectrum, the orders $O_X$ and $O_Y$ of the AR filters of bispectra of $X_i(t)$ and $Y_i(t)$ are the ranks of the super matrices $T_X$ and $T_Y$. Therefore, $O_X$ and $O_Y$ are chosen by using singular value decomposition. Having found the orders, we obtain the coefficients of the AR filters of the bispectra by solving the following linear system of equations:

$$\begin{pmatrix} R_{3z}(0) & R_{3z}(1) & \ldots & R_{3z}(O_z) \\ R_{3z}(-1) & R_{3z}(0) & \ldots & R_{3z}(O_z - 1) \\ \cdot & \cdot & \ldots & \cdot \\ \cdot & \cdot & \ldots & \cdot \\ \cdot & \cdot & \ldots & \cdot \\ R_{3z}(-O_z) & R_{3z}(-O_z + 1) & \ldots & R_{3z}(0) \end{pmatrix} \begin{pmatrix} 1 \\ b_{1z} \\ \cdot \\ \cdot \\ \cdot \\ b_{O_z z} \end{pmatrix} = \begin{pmatrix} \beta_z \\ 0 \\ \cdot \\ \cdot \\ \cdot \\ 0 \end{pmatrix},$$

$z = X$ or $Y.$ where the skewness ($\beta_z$) and the coefficients ($b_{1z}, \ldots, b_{O_z z}$), $z = X$ or $Y$, can be obtained by solving the linear system of equations.

The auto/cross bispectrum of $X_i(t)$ and $Y_i(t)$ are computed in step 926 as the cubic root of the triple product of the skewnesses $(\beta_X \beta_Y \beta_Y)^{\frac{1}{3}}$, divided by the triple product of the Fourier transforms of the AR filter coefficients ($H_z(f)$), i.e., $$BC(f_1, f_2) = (\beta_X \beta_Y \beta_Y)^{\frac{1}{3}} / H_X(f_1) H_X(f_2) H^*_Y(f_1 + f_2)$$

$$H_z(f) = 1 + \sum_{i=1}^{O_z} b_{iz} e^{-j2\pi f i}, z = X, Y.$$

and BR($f_1$, $f_2$) is the real triple product for that same signal:

$$BR(f_1, f_2) = P_X(f_1) * P_X(f_2) * P_Y(f_1 + f_2)$$

where the auto power spectra of $X_i(t)$ and $Y_i(t)$, $P_X(f)$ and $P_Y(f)$, are computed by squaring the magnitudes of transfer function of the AR filters for auto power spectra of $X_i(t)$ and $Y_i(t)$ ($H_{PX}(f)$ and $H_{PY}(f)$) respectively. If requested, the same normalization used in step 808 may be used here. Similarly, $(\beta_z)^{\frac{1}{3}}/H_z(f)$ is divided by the square root of the sum of the square of its magnitude for certain frequency band, its largest peak value, or some similarly derived normalizing constant.

After obtaining power spectrum and auto/cross bispectrum, the system computes the bispectral density array, the biphase, the bicoherence, and the square-rooted average real triple product (RTP) array in step 928 in the same way as in steps 826, 828, 830, and 832. In step 930, the system returns to the monitor module 402 the requested auto/cross power spectral density array, bispectral density, square-rooted real triple product, biphase, and bicoherence arrays.

The above parametric equations used to compute the auto/cross bispectral arrays can be generalized to compute auto/cross higher-order spectral arrays. This will allow the computation of the trispectrum, quadspectrum, etc. Assuming that the arrays for a Kth-order spectrum are to be computed the following equations can be used:

The auto/cross Kth-order spectrum:

$$KC(f_1, f_2, \ldots, f_{K-1}) = ((\beta_X)^{K-1} \beta_Y)^{1/K} / H_X(f_1) H_X(f_2) \ldots$$

$$H_X(f_{K-1}) H^*_Y(f_1 + f_2 + \ldots + f_{K-1})$$

$$H_z(f) = 1 + \sum_{i=1}^{O_z} b_{iz} e^{-j2\pi f i}, z = X, Y.$$

The real Kth-order product:

$$KR(f_1, f_2, \ldots, f_{K-1}) = P_X(f_1) * P_X(f_2) * \ldots * P_X(f_{K-1}) * P_Y(f_1 + f_2 + \ldots + f_{K-1})$$

After obtaining the auto/cross Kth-order spectrum, the system computes the auto/cross Kth-order spectral density array, the auto/cross Kth-order phase, and the auto/cross Kth-order coherence the same way as in the frequency-domain-based method.

Figure 10A:
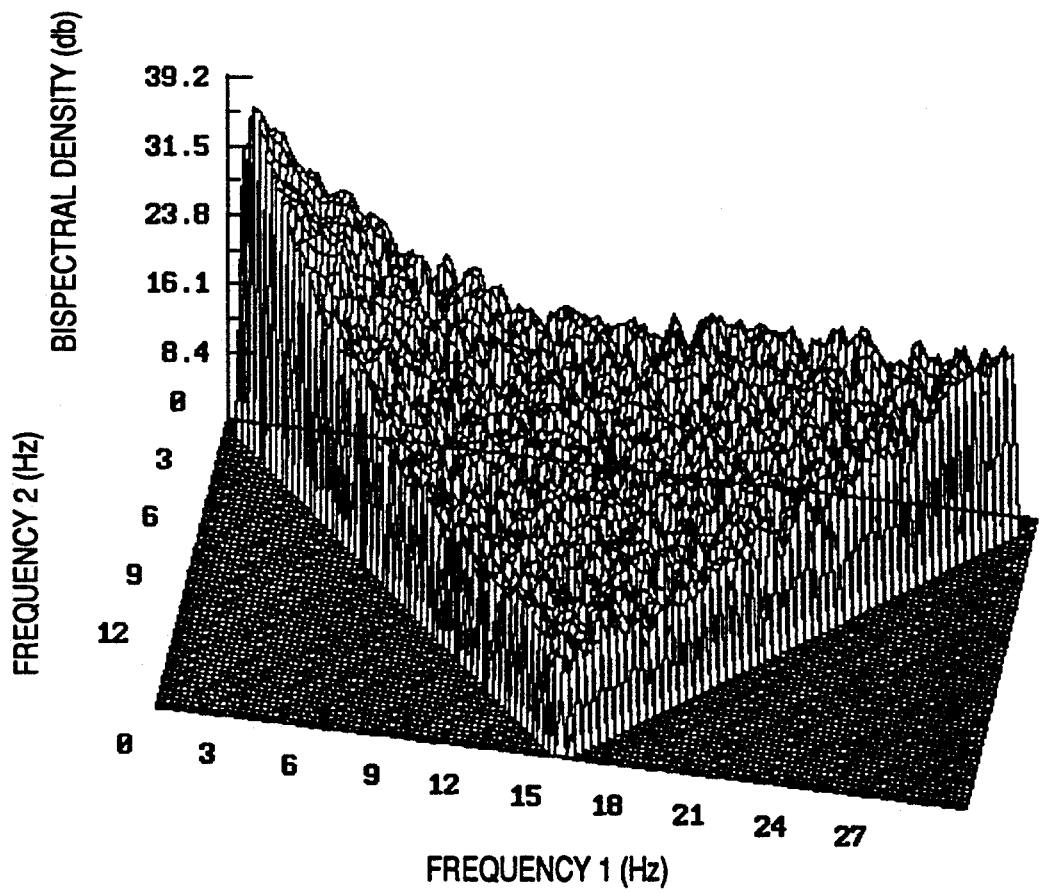
FIG. 10(a) is a graph showing a bispectral density array generated by the system of FIG. 1.
Figure 10B:
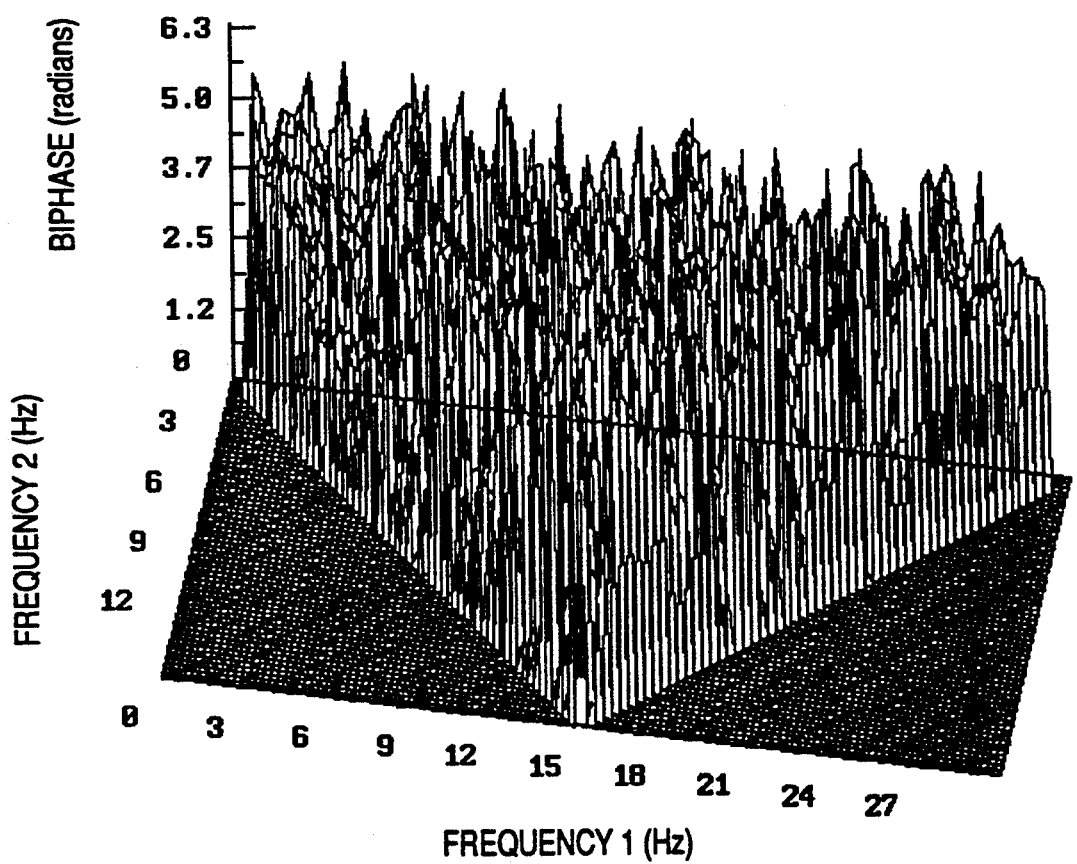
FIG. 10(b) is a graph showing a biphase array generated by the system of FIG. 1.
Figure 10C:
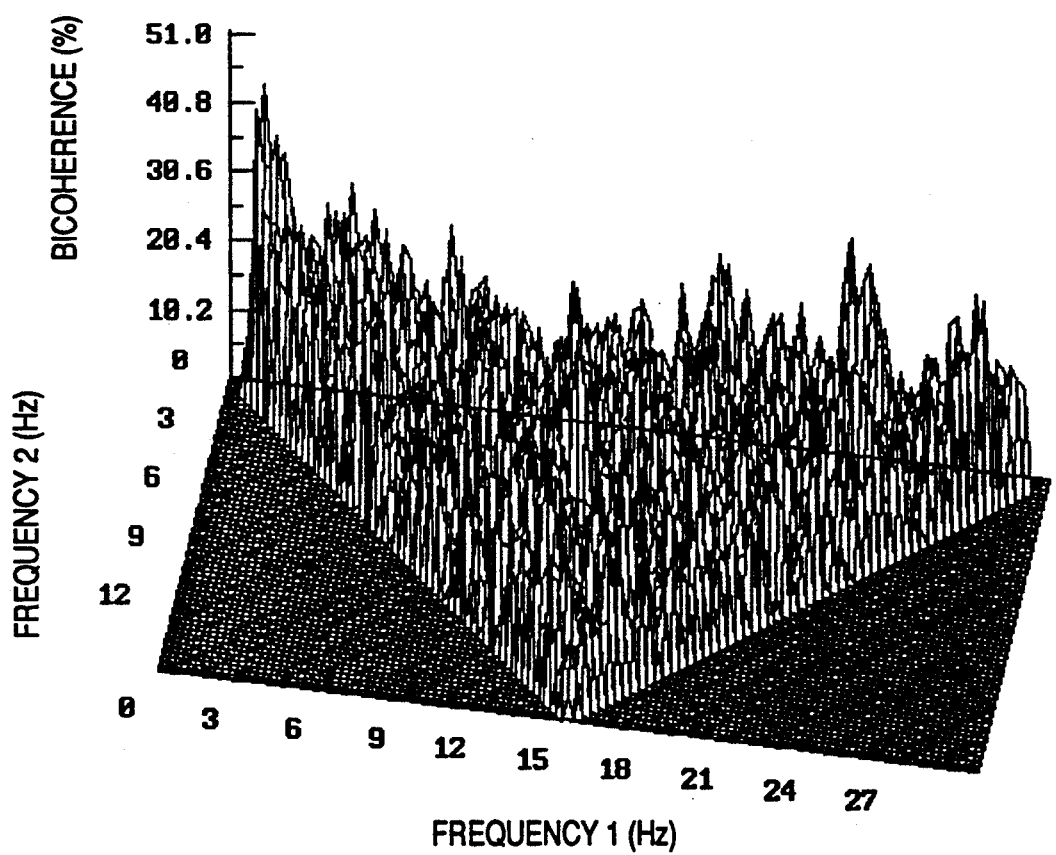
FIG. 10(c) is a graph showing a bicoherence array generated by the system of FIG. 1.
Figure 10D:
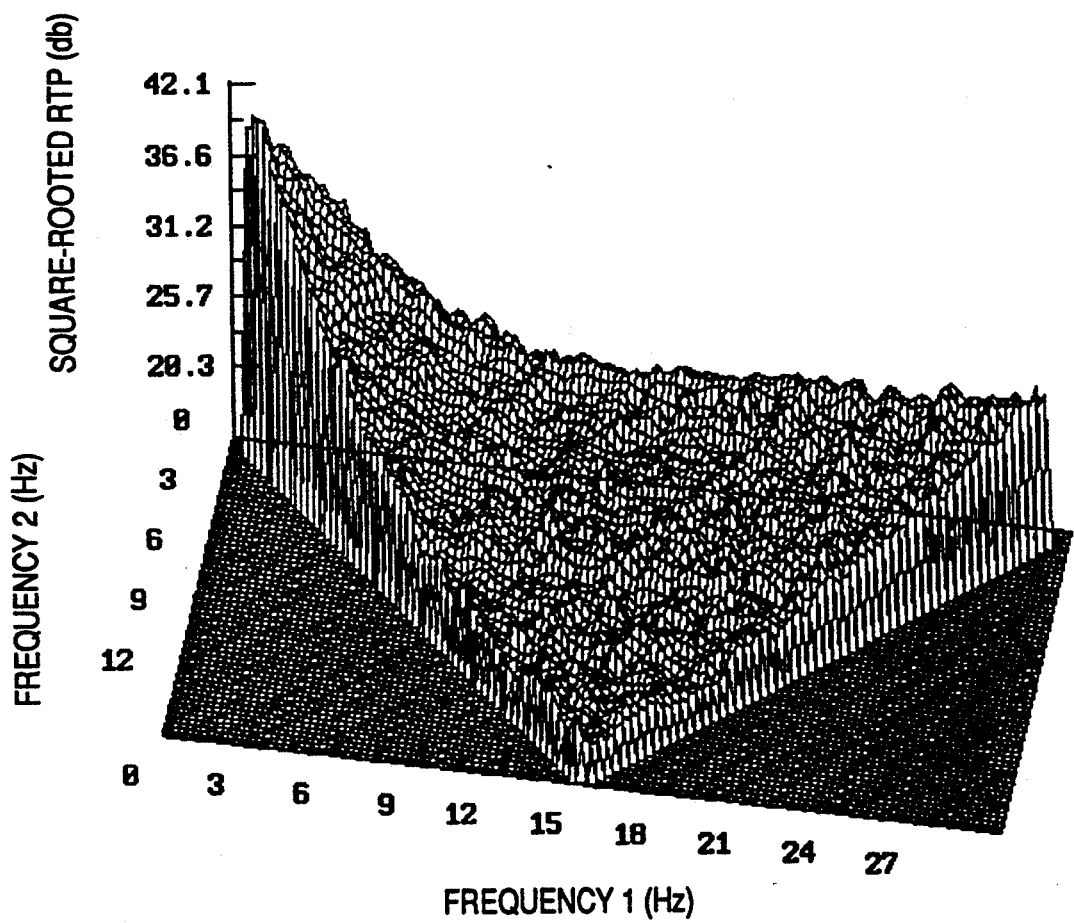
FIG. 10(d) is a graph showing an array of square root of real triple product generated by the system of FIG. 1.

For illustration purposes FIGS. 10(a)-10(c) are graphs sample autobispectral arrays showing frequency pairs 0<f$_1$<30 Hz, and 0<f$_2$<15 Hz. A bispectral density array is shown in FIG. 10(a) where the Z axis represents the magnitude in decibels (db) of the coupled interaction between all appropriate frequency pairs f$_1$ and f$_2$. Recall that the frequency pair (f$_1$, f$_2$) must adhere to the equation:

f$_1$+f$_2$<N/2 where N=256 Hz in this case. A bicoherence array is shown in FIG. 10(c) where the Z axis represents the normalized magnitude in percent (%) of the coupled interaction between all appropriate frequency pairs f$_1$ and f$_2$. A biphase array is shown in FIG. 10(b) where the Z axis represents the phase in radians of the coupled interaction between all appropriate frequency pairs f$_1$ and f$_2$. An array of square root of real triple product is shown in FIG. 10(d) where the Z axis represents the magnitude in decibels (db) of the coupled interaction between all appropriate frequency pairs f$_1$ and f$_2$.

Figure 11:
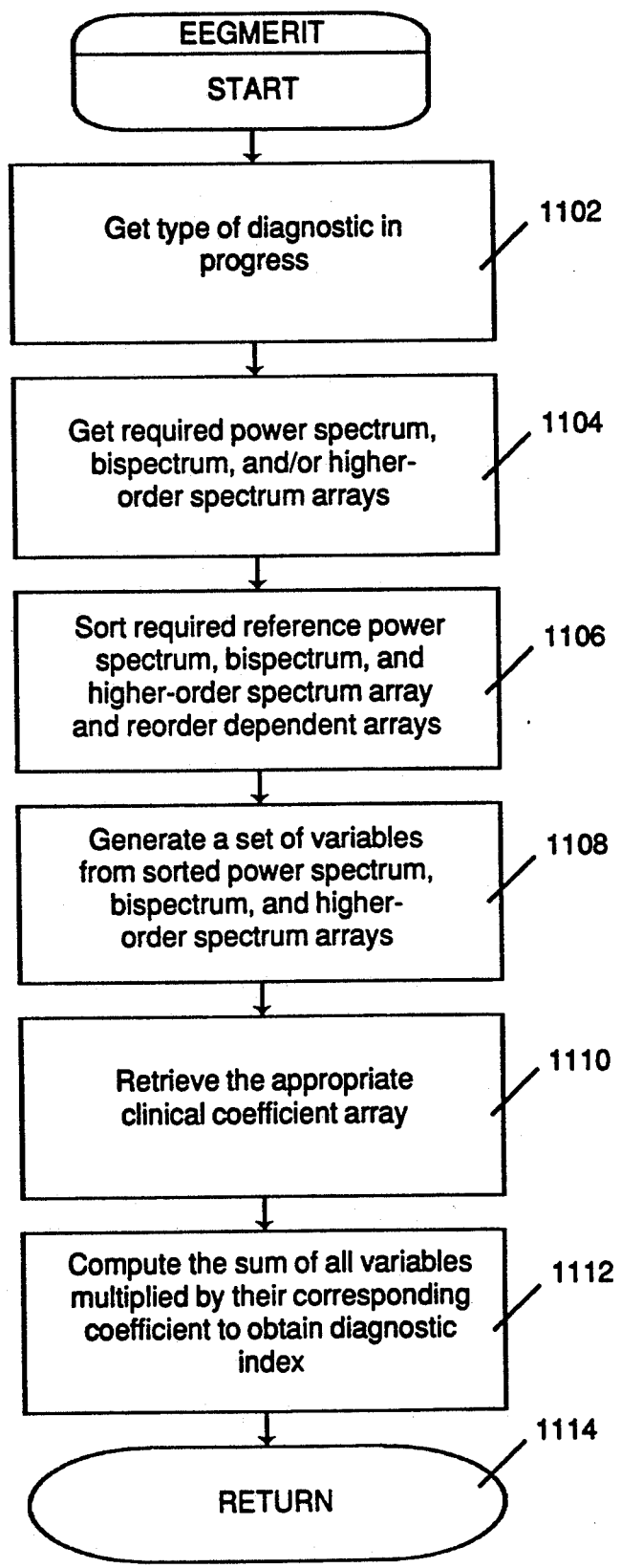
FIG. 11 is a flow chart of the operations of the diagnostic index derivation module shown in FIG. 4.

Referring to FIG. 11, a more detailed illustration of the diagnostic index generation module 410 will now be provided. In step 1102, the system identifies the type of diagnostic assessment in progress. In a preferred embodiment, the 5 possible options are:

1. Depth of anesthesia, consciousness, pain & surgical stress.
2. Cerebral ischemia and hypoxia.
3. Cerebral intoxication (alcohol, narcotics).
4. Evoked potential evaluation
5. Cognitive process evaluation In step 1104, the system gets the auto/cross power spectrum, bispectrum, and/or higher-order spectrum arrays that are required for the computation of the requested diagnostic index using the sorting method described below. The various arrays that can be used in the generation of the diagnostic index are: auto/cross power spectrum; auto/cross bispectral density; auto/cross bicoherence; auto/cross bispectral real product; auto/cross biphase; auto/cross Kth-order spectral density; auto/cross Kth-order coherence; auto/cross Kth-order spectral real product; and auto/cross Kth-order phase;

The sorting of auto/cross power spectrum, bispectrum, and higher-order spectrum arrays is an important feature of the present invention as it provides a mechanism to compensate for changes in the energy distribution in these (and any other) spectra. The following is a general description of how the feature is implemented in a preferred embodiment:

Based on an FFT derived from 4-second records, as described in the preferred embodiment, 120 data points can be computed for a power spectrum array that covers the frequency band 0–30 Hz (with 4-second records and a sampling rate of 128 samples per second, the resolution of the FFT is 0.25 Hz, and the range used is 30 Hz wide, thus there are 120=30 Hz/0.25 Hz data points). When the 120 data points are sorted in descending order, the first element in the sorted array will correspond to the largest power spectrum value, and the last element will correspond to the smallest power spectrum value. A distribution histogram of the power can then be generated using the sorted array. The X axis on the histogram will represent power in dbs and the Y axis will represent the number of points in the sorted array that correspond to a particular X axis power value. If all points in the sorted array are added together, the sum will represent the total power in the 0–30 Hz spectrum. If a number of adjacent points in the sorted array are added together, a portion of the histogram representing a percentage of total power is obtained. For example, in a particular EEG signal, the top 2 points in the sorted array represents the top 10% of the total power in the power distribution histogram. Similarly adding the bottom 70 points (for the same signal) in the sorted array will give the bottom 10% of the total power in the histogram. Given this approach any portion of the power distribution histogram can be obtained by adding adjacent elements in the sorted array (top 25% of total power, middle 50% of total power, etc.) (given that one has empirically determined the transfer function from specific points to percentage of total power).

By sorting, we are able to track regions of high activity and low activity (peaks and valleys) in the 0–30 Hz power spectrum without having to analyze specific narrow frequency bands. This is equivalent to mapping the power spectrum to its power distribution function and operating on fixed bands within that distribution function. This transformation addresses some of the inconsistencies in the behavior of EEG power observed when hypnotic anesthetic agents are administered. More generally, the sorting scheme outlined above will transform any auto/cross power spectrum, bispectrum, and higher-order spectrum array of any dimension, into a one-dimensional distribution function of the values it contains. The one dimensional distribution is then divided into fixed bands that can be combined to produce a univariate diagnostic index.

In step 1106, the reference auto/cross power spectrum, bispectrum, and higher-order spectrum arrays are sorted. The corresponding dependent arrays are reordered according to the sorted sequence of the reference array. A reference array is an array whose values are used as the primary sort key for a group of corresponding arrays that have the same number of variables and are identical in size to the reference array. For example, if the reference array were to have four elements and they were given the indices 1, 2, 3, 4 before sorting, and after the sort the new order of the indices were 2, 1, 4, 3 then one could use the same rearrangement to reorder any other array of the same size (in this case by placing the second element first, the first element second, etc.). In this way, one can use the sort of the reference array to rearrange the dependent arrays. In the preferred embodiment, the reference array is autobispectral density and the dependent arrays are autobicoherence and the square rooted average real triple product. Autobispectral density was selected as the reference array because it provides information about the residual power at each frequency pair after random phase cancellations. Thus, the sort of the autobispectral density array provides a more stable means to select autobicoherence and real triple product values than would the sort of those arrays themselves. A different array may be selected to satisfy other requirements.

In step 1108, the sorted auto/cross power spectrum, bispectrum, and higher-order spectrum arrays are each divided into bins as described earlier. The sum of the points in each bin for each array is computed and stored in a temporary variable. In step 1110, the clinically predetermined coefficient array for the desired diagnostic index is retrieved from resident memory (or from the storage device). Each coefficient in the predetermined coefficient array corresponds to one of the temporary variables generated in step 1108. In step 1112, the univariate diagnostic index is produced from the sum of all variables multiplied by their corresponding coefficients in the predetermined coefficient array. In step 1114, the program returns to the monitor module 402.

The predetermined clinical coefficient arrays referred to above are essential to the device's ability to achieve clinically relevant diagnostic efficacy. The process adopted for generating these clinical reference arrays will now be described. Since a large number of possible reference arrays must be generated to accommodate all the diagnostic modalities of the system, only one will be discussed in detail. All other reference arrays are generated in a similar fashion. For illustration purposes a method for generating the coefficients required to track depth of anesthesia using the derived signals FL and FR (of the preferred embodiment) is described below:

In order to determine the clinical coefficients for a particular diagnostic index, raw data as well as clinical diagnoses are required. In the particular case described below, in order to develop an index which indicates anesthetic depth, EEG signals and assessments of the patient's response to clinical stimuli were collected. In one case below, the assessment is based on the patient's change in arterial blood pressure. In the other case, the assessment is the surgeon's judgment as to whether the patient had a motor-reflexive response. Once the data have been obtained, the various spectra and variables as described above may be generated. By performing statistical regressions on the processed data in conjunction with the clinical diagnoses, the coefficients which produce the index with the best predictive diagnostic ability can be determined.

In two separate studies EEG potentials were continuously recorded from a group of patients undergoing elective surgery. The recording period started at approximately 5 minutes prior to induction and lasted for the duration of the surgery. The derived signals FL, FR, PL, PR, FPL and FPR were acquired using the procedure described above.

The purpose of the first study was to determine whether autobispectrum variables provide information about anesthetic depth at incision. Forty adult patients were studied. Anesthesia was induced with thiopental (up to 5.0 mg/kg) and intubation performed after the administration of succinylcholine. Patients were randomly assigned to receive isoflurane 0.75 MAC (Mean Alveolar Concentration), 1.00 MAC, or 1.25 MAC in 100% oxygen. End-tidal agent concentration was monitored and after a period of steady-state had been achieved, purposeful movement in response to skin incision was assessed. Each patient was classified as either a "mover" or a "non-mover" based on the patient's response to incision.

The purpose of the second study was to determine whether autobispectrum variables provide information about predicting hemodynamic responses to laryngoscopy during induction with sufentanil of alfentanil. Forty adult patients were studied. Patients received premedication with oral diazepam (0.05–0.15 mg/kg) and were induced with thiopental (4.0–6.0 mg/kg) and 60% nitrous oxide in oxygen, followed by vecuronium (0.1 mg/kg). Each patient was then randomly assigned to receive one of five dose regimens: normal saline; alfentanil 15 mcg/kg or 30 mcg/kg; sufentanil 0.5 mcg/kg or 1.5 mcg/kg. Laryngoscopy was performed 3 minutes after drug administration. Brachial blood pressure was measured every minute with a cuff device. Patients who exhibited a change in mean arterial pressure of more than 20% in response to intubation were classified as "responders"; those who did not exhibit such a change at intubation were classified as "non-responders."

An autobispectral density, an auto bicoherence, and an auto square-rooted average real triple product array were generated for the derived signals FL and FR for each patient using a two minute period prior to the stimulus. The frequency band for which the bispectral arrays were computed was 0.25–30 Hz. Each bispectral array contained 3600 data points.

The resultant auto bispectral density, auto bicoherence, and auto square-rooted average real triple product arrays were sorted using the auto bispectral density array as the sorting reference array. The sorting was done using the algorithm described above.

Eleven variables were produced from each of the sorted arrays as described below:

Var1 = Sum of the largest 15 points in sorted array
Var2 = Sum of points ranked 16th to 30th in sorted array
Var3 = Sum of points ranked 31st to 50th in sorted array
Var4 = Sum of points ranked 51th to 100th in sorted array
Var5 = Sum of points ranked 101th to 150th in sorted array
Var6 = Sum of points ranked 151th to 300th in sorted array
Var7 = Sum of points ranked 301th to 500th in sorted array
Var8 = Sum of points ranked 501st to 900th in sorted array
Var9 = Sum of points ranked 901st to 1500th in sorted array
Var10 = Sum of points ranked 1501st to 2400th in sorted array
Var11 = Sum of points ranked 2401st to 3600th in sorted array The values of the 11 variables for each array were computed. As a result, there were 33 temporary variables per patient per signal.

The 80 patients were then classified into two groups. The first group contained all the patients from the first study that moved at incision and all the patients from the second study that had a change in blood pressure of greater than 20% in response to intubation. The second had all patients from the first study who did not move at incision and all the patients from the second study that had a blood pressure response of less than 20% for intubation.

In order to produce a set of coefficients that would yield the most effective diagnostic index, a discriminant analysis was performed. The diagnostic index ($I(c_0, c_1, \ldots, c_{33})$) for a set of coefficients ($c_0, c_1, \ldots, c_{33}$) is given by:

$$I(c_0, c_1, \ldots c_{33}) = c_0 + (BIS_A * c_1 + \ldots + BIS_K * c_{11}) + (BIC_A * c_{12} + \ldots + BIC_K * c_{22}) + (PS_A * c_{23} + \ldots + PS_K * c_{33})$$

where $BIS_A$ through $BIS_K$ are the 11 sorted temporary variables from the bispectrum array; $BIC_A$ through $BIC_K$ are the variables from the bicoherence array; and $PS_A$ through $PS_K$ are the variables from the sorted square-rooted average real triple product array. The discriminant analysis, given the values of the temporary variables mentioned above and the responder/non-responder classification for each patient, produces the set of coefficients which yield the best separation of responders and non-responders by the function I. Discriminant analysis algorithms are publically available; in this case, the ones used are from the statistics library available from IMSL (Houston, Tex.). Below is a sample list of coefficients generated using a database of 170 patients:

| | for derived signals FL, FR |
|---|---|
| $c_0$ | −4.28 |
| $c_1$ | −0.65 |
| $c_2$ | +0.57 |
| $c_3$ | +1.21 |
| $c_4$ | −1.23 |
| $c_5$ | +2.63 |
| $c_6$ | −3.34 |
| $c_7$ | +2.11 |
| $c_8$ | +2.74 |
| $c_9$ | −3.08 |
| $c_{10}$ | 0.0 |
| $c_{11}$ | −0.66 |
| $c_{12}$ | +0.04 |
| $c_{13}$ | −1.86 |
| $c_{14}$ | +0.50 |
| $c_{15}$ | +0.14 |
| $c_{16}$ | −0.30 |
| $c_{17}$ | +0.15 |
| $c_{18}$ | −0.08 |
| $c_{19}$ | −0.11 |
| $c_{20}$ | +0.05 |
| $c_{21}$ | +0.05 |
| $c_{22}$ | −0.02 |
| $c_{23}$ | +0.67 |

| | for derived signals FL, FR |
|---|---|
| $C_{24}$ | −1.02 |
| $C_{25}$ | 0.0 |
| $C_{26}$ | −0.19 |
| $C_{27}$ | −1.27 |
| $C_{28}$ | +1.20 |
| $C_{29}$ | +1.25 |
| $C_{30}$ | −2.15 |
| $C_{31}$ | −2.43 |
| $C_{32}$ | +3.16 |
| $C_{33}$ | +0.64 |

For the two studies discussed above the univariate index was used to predict the response to the stimulus for each patient. The following is a summary of the results achieved:

| | |
|---|---|
| Sensitivity; predicting movement at incision = | 96% |
| Specificity; predicting no movement at incision = | 63% |
| Overall accuracy; predicting move/no move at incision = | 83% |
| Sensitivity; predicting >20% BP change at intubation = | 100% |
| Specificity; predicting <20% BP change at intubation = | 50% |
| Overall accuracy; predicting BP change at intubation = | 85% |

The example above shows one approach to obtaining a set of coefficients for a diagnostic application in a retrospective manner. Several other approaches can be used to separate the clinical population being studies using a univariate index. Such approaches include but are not limited to linear regression, stepwise linear regression, logistic regression, and stepwise logistic regression. Of course regardless of which method is used to retrospectively compute the coefficients, performance of the final index must be confirmed in a prospective trial prior to using it in patient care.

The analytic process described above is used to generate the reference databases for cerebral ischemia, cerebral hypoxia, consciousness, degrees of intoxication, altered evoked potential responses, and normal or abnormal cognitive processes including but not limited to identifying patients with Alzheimer's disease and HIV-related dementias.

In addition to quantifying the depth, adequacy of anesthesia, and pain responses during surgical stress, the system and method of the present invention may also be used to assess a myriad of cerebral phenomena that alter the nonlinear frequency structure of the EEG as quantified by bispectrum and higher-order spectrum approaches. Such cerebral phenomena include but are not limited to, cerebral ischemia, cerebral hypoxia, level of consciousness, degree of cerebral intoxication, altered evoked potential responses, and normal or abnormal cognitive processes caused by neurological disorders like Alzheimer's disease or HIV-related dementias.

Although power spectrum and bispectrum analysis techniques have been applied to the EEG signal for diagnostic purposes, as was discussed in the background above, higher-order spectral approaches have never been used. Furthermore no power spectrum, bispectrum, or higher-order spectrum technique has ever been used in conjunction with the sorting method described above. Specifically, the system and method of the present invention sort various auto/cross power spectrum, bispectrum, and higher-order spectrum arrays, divides the sorted arrays into bins, sums the variables in each bin, multiplies the value from each bin by a clinically derived coefficient, and finally adds all variables together to generate a univariate diagnostic index. The different arrays that can be used are: auto/cross power spectrum, auto/cross bispectral density, auto/cross bicoherence, auto/cross biphase, auto/cross average real triple product, auto/cross Kth-order spectral density, auto/cross Kth-order coherence, auto/cross phase, and auto/cross real product.

While the foregoing invention has been described with reference to its preferred embodiments, various alterations and modifications will occur to those skilled in the art. All such alterations and modifications are intended to fall within the scope of the appended claims.

We claim:

1. A method of noninvasively detecting cerebral phenomena comprising the steps of:
   acquiring electroencephalographic signals through at least one electrode from a body surface of a subject being analyzed;
   band pass filtering said electroencephalographic signals to obtain filtered signals in a desired frequency range;
   dividing said filtered signals into a plurality of data records;
   characterizing dynamic phase relations within said filtered signals by processing said filtered signals to generate Kth-order spectral values, where K is an integer greater than 2;
   deriving from said generated Kth-order spectral values, a diagnostic index that quantifies the detected cerebral phenomena.

2. The method of noninvasively detecting cerebral phenomena of claim 1 wherein the step of acquiring electroencephalographic signals further comprises the step of attaching electrodes to a head of the subject being analyzed in order to obtain a unipolar electroencephalographic signal from each region of interest of both left and right hemispheres of the subject's brain to which said electrodes are attached.

3. The method of noninvasively detecting cerebral phenomena of claim 1 wherein said Kth-order spectral values generated in said step of characterizing said dynamic phase relations are auto Kth-order spectral density values.

4. The method of noninvasively detecting cerebral phenomena of claim 1 wherein said Kth-order spectral values generated in said step of characterizing said dynamic phase relations are auto Kth-order coherence values.

5. The method of noninvasively detecting cerebral phenomena of claim 1 wherein said Kth-order spectral values generated in said step of characterizing said dynamic phase relations are auto Kth-order phase values.

6. The method of noninvasively detecting cerebral phenomena of claim 1 wherein said step of acquiring electroencephalographic signals further comprises the step of attaching electrodes to the head of the subject being analyzed in order to obtain bipolar data sets of electroencephalographic signals from left and right hemispheres of the subject's brain to which said electrodes are attached.

7. The method of noninvasively detecting cerebral phenomena of claim 6 wherein one bipolar data set is acquired from a n frontal left hemisphere of the subject's brain and another bipolar data set is acquired from a frontal right hemisphere of the subject's brain.

8. The method of noninvasively detecting cerebral phenomena of claim 6 wherein one bipolar data set is acquired from a left occipital region of the subject's brain and another bipolar data set is acquired from a right occipital region of the subject's brain.

9. The method of noninvasively detecting cerebral phenomena of claim 6 wherein one bipolar data set is acquired from a left parietal region of the subject's brain and another bipolar data set is acquired from a right parietal region of the subject's brain.

10. The method of noninvasively detecting cerebral phenomena of claim 1 wherein said Kth-order spectral values generated in said step of characterizing said dynamic phase relations are cross Kth-order spectral density values.

11. The method of noninvasively detecting cerebral phenomena of claim 1 wherein said Kth-order spectral values generated in said step of characterizing said dynamic phase relations are cross Kth-order coherence values.

12. The method of noninvasively detecting cerebral phenomena of claim 1 wherein said Kth-order spectral values are generated in said step of characterizing said dynamic phase relations are cross Kth-order phase values.

13. The method of noninvasively detecting cerebral phenomena of claim 1 wherein the cerebral phenomena being detected are pain responses during surgical stress in the subject being analyzed.

14. The method of noninvasively detecting cerebral phenomena of claim 1 wherein the physical phenomenon being detected is the degree of cerebral intoxication of the subject being analyzed.

15. The method of noninvasively detecting cerebral phenomena of claim 1 wherein the cerebral phenomena being detected are normal or abnormal cognitive processes of a subject being analyzed.

16. The method of noninvasively detecting cerebral phenomena of claim 1 wherein the cerebral phenomenon being detected is chronic ischemia or infarction in the subject being analyzed.

17. The method of noninvasively detecting cerebral phenomena of claim 1 wherein the cerebral phenomenon being detected are cognitive processes caused by neurological disorders.

18. The method of noninvasively detecting cerebral phenomena of claim 1 wherein the cerebral phenomenon being detected are altered evoked potential responses.

19. The method of noninvasively detecting cerebral phenomena of claim 18 wherein said step of acquiring electorencephalographic signals comprises acquiring electorencephalographic signals through at least one electrode placed near areas of the brain in which the evoked potential response occurs.

20. The method of noninvasively detecting cerebral phenomena of claim 18 wherein said step of acquiring electorencephalographic signals comprises acquiring electorencephalographic signals from one complete evoked potential response.

21. The method of noninvasively detecting cerebral phenomena of claim 1 wherein said Kth-order spectral values generated in said step of characterizing said dynamic phase relations are average auto Kth-order complex product values.

22. The method of noninvasively detecting cerebral phenomena of claim 1 wherein said Kth-order spectral values generated in said step of characterizing said dynamic phase relations are average cross Kth-order real product values.

23. The method of noninvasively detecting cerebral phenomena of claim 1 wherein said Kth-order spectral values generated in said step of characterizing said dynamic phase relations are average cross Kth-order complex product values.

24. The method of noninvasively detecting cerebral phenomena of claim 1 wherein said Kth-order spectral values generated in said step of characterizing said dynamic phase relations are average auto Kth-order real product values.

25. A system for noninvasively detecting cerebral phenomena comprising:
means for acquiring electroencephalographic signals through at least one electrode from a body surface of a subject being analyzed;
means for band pass filtering said electroencephalographic signals to eliminate those signals outside a desired frequency range;
means for dividing said filtered signals into a plurality of data records;
means for generating Kth-order spectral values capable of characterizing dynamic phase relations within said filtered electroencephalographic signals where K is an integer greater than 2;
means for deriving a diagnostic index that quantifies the detected cerebral phenomena.

26. The system for noninvasively detecting cerebral phenomena of claim 25 further comprising a plurality of said means for acquiring electroencephalographic signals, each of said means for acquiring electroencephalographic signals being connected to said means for filtering.

27. The system for noninvasively detecting cerebral phenomena of claim 26 wherein said plurality of said means for acquiring electroencephalographic signals is a plurality of electrodes attachable to a head of a subject being analyzed to obtain a unipolar electroencephalographic signal from each of a plurality of regions of interest on both left and right hemispheres of the subject's brain.

28. The system for noninvasively detecting cerebral phenomena of claim 25 wherein said means for acquiring electroencephalographic signals comprises:
a plurality of surface electrodes for mounting on a surface of a head of the subject being analyzed;
means for providing defibrillator protection for limiting voltage to said amplifier during a discharge;
means for amplifying said filtered signals for a high gain in order to maximize the dynamic range for high frequency, low energy wave components of said filtered signals;
means for feeding said signals to an analog-to-digital converter to convert said signals to digital signals.

29. The system for noninvasively detecting cerebral phenomena of claim 25 wherein said Kth-order spectral values are auto Kth-order spectral density values and further comprising means for organizing said auto Kth-order spectral density values in at least one array of auto Kth-order spectral density values.

30. The system for noninvasively detecting cerebral phenomena of claim 25 wherein said means for acquiring electroencephalographic signals from different regions of a brain of said subject.

31. The system for noninvasively detecting cerebral phenomena of claim 25 wherein said means for generating Kth-order spectral values comprises means for computing auto Kth-order phase values.

32. The system of noninvasively detecting cerebral phenomena of claim 25 wherein said means for generating Kth-order spectral values comprises means for computing auto Kth-order coherence values.

33. The system for noninvasively detecting cerebral phenomena of claim 25 wherein said means for generating Kth-order spectral values comprises means for computing an average auto Kth-order real product.

34. The system for noninvasively detecting cerebral phenomena of claim 25 wherein said means for generating Kth-order spectral values comprises means for computing an average auto Kth-order complex product.

35. The system for noninvasively detecting cerebral phenomena of claim 25 wherein said means for generating Kth-order spectral values comprises means for computing cross Kth-order spectral density values.

36. The system for noninvasively detecting cerebral phenomena of claim 25 wherein said means for generating Kth-order spectral values comprises means for computing cross Kth-order coherence values.

37. The system for noninvasively detecting cerebral phenomena of claim 25 wherein said means for generating Kth-order spectral values comprises means for computing cross Kth-order phase values.

38. The system for noninvasively detecting cerebral phenomena of claim 25 wherein said means for generating Kth-order spectral values comprises means for computing an average cross Kth-order real product.

39. The system for noninvasively detecting cerebral phenomena of claim 25 wherein said means for generating Kth-order spectral values comprises means for computing an average cross Kth-order complex product.

40. A method of generating a diagnostic index for quantifying the presence or absence of a phenomena which is represented by spectral values generated from acquired electrical signals of the phenomena, said method comprising the steps of:
sorting said spectral values into predetermined bins of ranges of spectral values;
summing all of the spectral values in each bin;
multiplying the sum of spectral values in each bin by a predetermined coefficient to obtain a bin product;
summing said bin products to obtain a diagnostic index which represents a degree of presence or absence of said phenomena.

41. The method of generating a diagnostic index of claim 40 wherein said acquired electrical signals are electroencephalographic signals.

42. A system for generating a diagnostic index for quantifying the presence or absence of a phenomena which is represented by spectral values generated from acquired electrical signals of the phenomena, said system comprising:
means for sorting said spectral values into predetermined bins of ranges of spectral values;
means for summing all of the spectral values in each bin;
means for multiplying the sum of spectral values in each bin by a predetermined coefficient to obtain a bin product;
means for summing said bin products to obtain a diagnostic index which represents a degree of presence or absence of said phenomena.

43. The system for generating a diagnostic index of claim 42 wherein said acquired electrical signals are electroencephalographic signals.

44. A method of noninvasively detecting cerebral phenomena comprising the steps of:
acquiring electroencephalographic signals through at least one electrode from a body surface of a subject being analyzed;
band pass filtering said electroencephalographic signals to obtain filtered signals in a desired frequency range;
dividing said filtered signals into a plurality of data records;
characterizing dynamic phase relations within said filtered signals by processing said filtered signals to generate third-order moment values;
deriving from said generated third-order moment values, a diagnostic index that quantifies the detected cerebral phenomena.

45. A system for noninvasively detecting cerebral phenomena comprising:
means for acquiring electroencephalographic signals through at least one electrode from a body surface of a subject being analyzed;
means for band pass filtering said electroencephalographic signals to eliminate those signals outside a desired frequency range;
means for dividing said filtered signals into a plurality of data records;
means for generating third-order moment values capable of characterizing dynamic phase relations within said filtered electroencephalographic signals;
means for deriving a diagnostic index that quantifies the detected cerebral phenomena.

* * * * *